(12) United States Patent
Kim et al.

(10) Patent No.: US 12,390,120 B2
(45) Date of Patent: Aug. 19, 2025

(54) BIO-PROCESSOR, BIO-SIGNAL DETECTING SYSTEM, AND OPERATION METHOD OF BIO-PROCESSOR

(71) Applicant: Samsung Electronics Co., Ltd., Suwon-si (KR)

(72) Inventors: Junho Kim, Yongin-si (KR); Byungki Moon, Seoul (KR); Myoungoh Ki, Seongnam-si (KR); Jangbeom Yang, Suwon-si (KR); Seoungjae Yoo, Seongnam-si (KR); InChun Lim, Hwaseong-si (KR); Yuncheol Han, Yongin-si (KR); KeeMoon Chun, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1065 days.

(21) Appl. No.: 17/373,949

(22) Filed: Jul. 13, 2021

(65) Prior Publication Data

US 2021/0338095 A1 Nov. 4, 2021

Related U.S. Application Data

(63) Continuation of application No. 15/985,010, filed on May 21, 2018, now Pat. No. 11,083,392.

(30) Foreign Application Priority Data

Jul. 13, 2017 (KR) .................. 10-2017-0089143
Nov. 13, 2017 (KR) .................. 10-2017-0150733

(51) Int. Cl.
*A61B 5/0533* (2021.01)
*A61B 5/00* (2006.01)
(Continued)

(52) U.S. Cl.
CPC .......... *A61B 5/0533* (2013.01); *A61B 5/0537* (2013.01); *A61B 5/4872* (2013.01);
(Continued)

(58) Field of Classification Search
CPC ..... A61B 5/0533; A61B 5/0537; A61B 5/053; A61B 5/0531; A61B 5/7221; A61B 5/6802
See application file for complete search history.

(56) References Cited

U.S. PATENT DOCUMENTS 4,318,412 A * 3/1982 Stanly ................. A61B 5/0006
600/508
5,063,937 A * 11/1991 Ezenwa .............. A61B 5/0535
600/536
(Continued)

FOREIGN PATENT DOCUMENTS

CN 103598886 A 2/2014
CN 105997072 A 10/2016
(Continued)

*Primary Examiner* — Sean P Dougherty
(74) *Attorney, Agent, or Firm* — Harness, Dickey & Pierce, P.L.C.

(57) ABSTRACT

A bio-processor, a bio-signal detecting system, and an operation method of the bio-processor are provided. The bio-processor includes a bioelectrical impedance sensor and a digital signal processor. The bioelectrical impedance sensor measures bioelectrical impedance during a sensing time including a portion of a settling time. The digital signal processor estimates a settled bioelectrical impedance value based on changes in the measured bioelectrical impedance. The digital signal processor generates bio-data based on the settled bioelectrical impedance value. The bio-processor reduces a time when a bio-signal is measured and ensures accuracy of the settled bioelectrical impedance value.

20 Claims, 12 Drawing Sheets

(51) Int. Cl.
  *A61B 5/053* (2021.01)
  *A61B 5/0531* (2021.01)
  *A61B 5/0537* (2021.01)
  *G01N 27/327* (2006.01)

(52) U.S. Cl.
  CPC ............ *A61B 5/053* (2013.01); *A61B 5/0531* (2013.01); *A61B 5/6824* (2013.01); *A61B 5/7203* (2013.01); *A61B 5/7221* (2013.01); *A61B 2560/0228* (2013.01); *A61B 2560/0238* (2013.01); *A61B 2560/0276* (2013.01); *A61B 2562/0209* (2013.01); *G01N 27/3274* (2013.01)

(56) References Cited

U.S. PATENT DOCUMENTS

| | | | | |
|---|---|---|---|---|
| 5,817,031 | A * | 10/1998 | Masuo | A61B 5/1075 600/547 |
| 6,370,425 | B1 * | 4/2002 | Oguma | A61B 5/4872 600/547 |
| 6,532,384 | B1 * | 3/2003 | Fukuda | A61B 5/0537 600/587 |
| 7,313,435 | B2 * | 12/2007 | Nakada | A61B 5/0537 600/547 |
| 7,317,320 | B2 * | 1/2008 | Park | A61B 5/4872 324/696 |
| 7,423,438 | B2 | 9/2008 | Park et al. | |
| 7,813,794 | B2 * | 10/2010 | Oku | A61B 5/0537 600/547 |
| 8,386,028 | B2 * | 2/2013 | Cha | A61B 5/0537 600/301 |
| 8,798,698 | B2 * | 8/2014 | Kim | A61B 5/0531 600/310 |
| 10,321,844 | B2 | 6/2019 | Varsavsky et al. | |
| 10,874,324 | B2 * | 12/2020 | Boverman | A61B 5/053 |
| 2002/0125408 | A1 | 9/2002 | Hosier et al. | |
| 2003/0109798 | A1 * | 6/2003 | Kermani | G01N 33/54373 600/547 |
| 2003/0122551 | A1 * | 7/2003 | Male | G01R 27/02 324/607 |
| 2003/0147115 | A1 | 8/2003 | Takizawa et al. | |
| 2004/0131198 | A1 * | 7/2004 | Watanabe | G01R 29/0821 381/71.7 |
| 2004/0172080 | A1 * | 9/2004 | Stadler | A61B 5/4875 607/17 |
| 2004/0181164 | A1 * | 9/2004 | Smith | A61B 5/053 600/547 |
| 2005/0101878 | A1 * | 5/2005 | Daly | A61N 1/36038 600/554 |
| 2005/0209528 | A1 * | 9/2005 | Sato | A61B 5/6887 600/547 |
| 2005/0278160 | A1 * | 12/2005 | Donnelly | G06F 30/367 703/19 |
| 2006/0229527 | A1 * | 10/2006 | Takehara | A61B 5/4872 600/547 |
| 2007/0072169 | A1 * | 3/2007 | Peyvan | G01R 19/0092 205/777.5 |
| 2008/0262375 | A1 * | 10/2008 | Brown | A61B 5/053 600/547 |
| 2008/0306402 | A1 * | 12/2008 | Singer | A61B 5/0537 600/547 |
| 2009/0043221 | A1 * | 2/2009 | Kaplan | A61B 5/6843 600/544 |
| 2010/0141380 | A1 | 6/2010 | Pishva | |
| 2010/0177205 | A1 | 7/2010 | Shimoda et al. | |
| 2011/0015503 | A1 * | 1/2011 | Joffe | A61B 5/30 600/383 |
| 2011/0105922 | A1 * | 5/2011 | Patangay | A61B 5/1118 600/508 |
| 2012/0016254 | A1 * | 1/2012 | Masuo | A61B 5/0809 600/547 |
| 2012/0157798 | A1 * | 6/2012 | Averina | A61N 1/36542 600/301 |
| 2013/0127774 | A1 * | 5/2013 | Hong | G06F 3/0446 345/174 |
| 2013/0284370 | A1 * | 10/2013 | Collins | H01J 37/32174 156/345.28 |
| 2013/0328572 | A1 * | 12/2013 | Wang | G01N 33/96 324/601 |
| 2014/0219463 | A1 * | 8/2014 | Poulsen | H04R 5/04 381/58 |
| 2014/0275845 | A1 * | 9/2014 | Eagon | A61B 5/6826 600/301 |
| 2015/0018632 | A1 * | 1/2015 | Khair | A61N 1/36585 607/18 |
| 2015/0042360 | A1 * | 2/2015 | Graner | G01N 27/02 324/630 |
| 2015/0164354 | A1 * | 6/2015 | Parker | A61B 5/7285 600/554 |
| 2015/0282725 | A1 * | 10/2015 | Single | A61N 1/36142 600/393 |
| 2015/0313487 | A1 * | 11/2015 | Single | A61B 5/24 600/554 |
| 2016/0007878 | A1 * | 1/2016 | Leuthardt | A61B 5/6825 600/301 |
| 2016/0089053 | A1 * | 3/2016 | Lee | A61B 5/0537 600/384 |
| 2016/0106337 | A1 * | 4/2016 | Jung | A61B 5/681 600/547 |
| 2016/0113578 | A1 * | 4/2016 | Eom | A61B 5/742 600/547 |
| 2016/0143591 | A1 * | 5/2016 | Bracke | A61N 1/0476 600/373 |
| 2016/0198977 | A1 * | 7/2016 | Eom | A61B 5/02416 600/300 |
| 2016/0220143 | A1 * | 8/2016 | Jung | A61B 5/4872 |
| 2016/0249857 | A1 * | 9/2016 | Choi | A61B 5/4872 600/547 |
| 2017/0049352 | A1 * | 2/2017 | Mirov | A61B 5/6843 |
| 2017/0100052 | A1 * | 4/2017 | Jung | A61B 5/02438 |
| 2017/0172448 | A1 | 6/2017 | Shin et al. | |
| 2017/0367600 | A1 * | 12/2017 | Pemberton | A61B 5/339 |
| 2018/0123704 | A1 * | 5/2018 | Yoo | H04L 27/26524 |
| 2018/0263521 | A1 * | 9/2018 | Stordopoulos | A61B 5/316 |
| 2019/0282152 | A1 * | 9/2019 | Ouwerkerk | A61B 5/681 |
| 2020/0183514 | A1 * | 6/2020 | Ramani | G06F 3/0219 |
| 2024/0197249 | A1 * | 6/2024 | Koskimäki | A61B 5/053 |

FOREIGN PATENT DOCUMENTS

| | | |
|---|---|---|
| JP | 2007-294552 A | 11/2007 |
| JP | 2010-169709 A | 8/2010 |
| KR | 10-2016-0094219 A | 8/2016 |
| KR | 10-2016-0098332 A | 8/2016 |
| KR | 20170074039 A | 6/2017 |

* cited by examiner

BIO-PROCESSOR, BIO-SIGNAL DETECTING SYSTEM, AND OPERATION METHOD OF BIO-PROCESSOR

CROSS-REFERENCE TO RELATED APPLICATIONS

This application is a continuation application of U.S. application Ser. No. 15/985,010, filed on May 21, 2018, which claims priority under 35 U.S.C. § 119 to Korean Patent Provisional Application No. 10-2017-0089143 filed Jul. 13, 2017, in the Korean Intellectual Property Office, and Korean Patent Application No. 10-2017-0150733 filed Nov. 13, 2017, in the Korean Intellectual Property Office, the entire contents of each of which are hereby incorporated by reference.

BACKGROUND

Example embodiments of the inventive concepts described herein relate to processing bio-signals. For example, at least some example embodiments relate to, a bio-processor, a bio-signal detecting system, and/or an operation method of the bio-processor.

With the development of medical technologies, human life has been increased. As food information, medical information, health care information, and the like for leading healthy lives have been provided in various manners, there has been a growing interest in physical examination such as examination of body fat. For this purpose, a variety of electronic devices for simplifying detection of bio-signals and analysis of body composition based on the detected bio-signals have been developed.

Recently, a method for measuring and processing bio-signals using a wearable device may be utilized to check healthy states of human bodies such as body fat. The wearable device is worn on a user anytime and anywhere and may detect bio-signals and may process the bio-signals. Further, since a bio-processor included in the wearable device is an element that performs analysis of the bio-signals, a speed and accuracy associated with the bio-processor processing the bio-signal may increase in importance.

A conventional bio-processor may wait until a bio-signal provided from a user is settled and may analyze body composition based on the settled bio-signal. Until a bio-signal is settled, the user may be forced to maintain a contact state with an electronic device and also minimize motion. If a time until the bio-signal settles is long, the user may need to limit motion for a relatively long period of time and accuracy of the bio-signal may be reduced due to, for example, the user sweating during this relatively long period of time.

SUMMARY

Example embodiments of the inventive concepts provide a bio-processor for reducing a time when a bio-signal is measured and increasing accuracy of analyzed bio-data, a bio-signal detecting system, and/or an operation method of the bio-processor.

According to an example embodiment, a bio-processor may include a bioelectrical impedance sensor configured to measure a measured bioelectrical impedance during a sensing time such that the sensing time includes a portion of a settling time, the settling time being prior to the measured bioelectrical impedance reaching a settled bioelectrical impedance value; and a digital signal processor configured to, estimate the settled bioelectrical impedance value based on changes in the measured bioelectrical impedance, and generate bio-data based on the settled bioelectrical impedance value.

According to another example embodiment, a bio-signal detecting system may include an electrode device configured to supply an output current to outside the bio-signal detecting system, and to receive a sensing voltage based on the output current; a bioelectrical impedance sensor configured to sense the sensing voltage during a sensing time, and to measure changes in bioelectrical impedance corresponding to the sensing voltage, the sensing time including a portion of a settling time, the settling time being prior to the bioelectrical impedance reaching a settled bioelectrical impedance value; and a processor configured to estimate the settled bioelectrical impedance value based on the measured changes in the bioelectrical impedance.

According to another example embodiment, an operation method of a bio-processor may include measuring a sensing voltage during a portion of a settling time, the settling time being prior to a value of a bioelectrical impedance reaching a settled bioelectrical impedance value; modeling the value of the bioelectrical impedance for the settling time in a fitting function based on changes in the sensing voltage to generate a modeled fitting function; estimating the settled bioelectrical impedance value at a settled time based on the modeled fitting function, the settled time being after expiration of the settling time; and generating bio-data based on the estimated bioelectrical impedance value.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, some example embodiments of the inventive concepts are described for clarity and in detail so that this disclosure will be thorough and complete and will fully convey the scope of example embodiments the inventive concepts to those skilled in the art.

Figure 1:
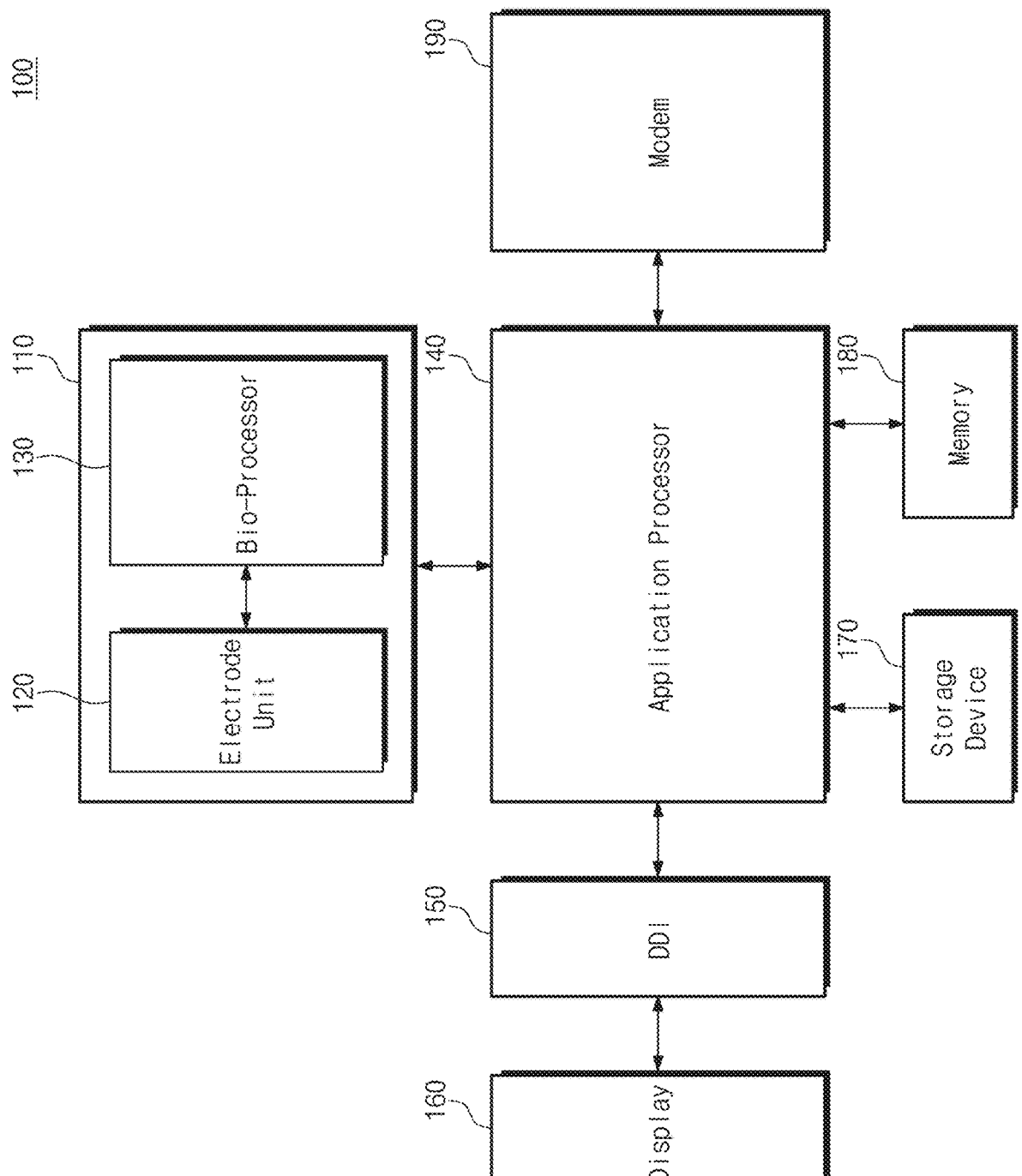
FIG. 1 is a block diagram illustrating a configuration of a bio-signal detecting system according to an example embodiment of the inventive concepts.

FIG. 1 is a block diagram illustrating a configuration of a bio-signal detecting system according to an example embodiment of the inventive concepts.

Referring to FIG. 1, a bio-signal detecting system 100 may include, but is not limited to, a wearable device. For example, the bio-signal detecting system 100 may include various portable electronic devices.

The bio-signal detecting system 100 may include a bio-signal detecting device 110, an application processor 140, a display driver integrated circuit (DDI) 150, a display 160, a storage device 170, a memory 180, and a modem 190.

The bio-signal detecting device 110 may include an electrode unit 120 and a bio-processor 130. The electrode unit 120 may include a plurality of electrodes. The plurality of electrodes may be configured to be in contact with a user to sense a bio-signal. For example, some of the plurality of electrodes may supply an output current to the user, and the other electrodes may receive a sensing voltage from the user. Hereinafter, a target which is in contact with the electrode unit 120 may be called a user. However, example embodiments are not limited thereto. For example, the target which is in contact with the electrode unit 120 may include a variety of objects such as an animal.

The bio-processor 130 may receive a bio-signal from the electrode unit 120 and may analyze the received bio-signal. For example, the bio-processor 130 may receive a sensing voltage from the electrode unit 120. The bio-processor 130 may measure bioelectrical impedance based on the sensing voltage and the output current supplied to the electrode unit 120. The bio-processor 130 may generate bio-data based on the measured bioelectrical impedance. For example, the bio-data may be body fat data. The bio-processor 130 may use user data for a height, a weight, an age, and/or a gender of a user to generate the body fat data. Such user data may be stored (e.g., in advance) in the bio-processor 130.

The bio-processor 130 may determine a sensing time for measuring bioelectrical impedance. The bio-processor 130 may measure bioelectrical impedance based on a sensing voltage received during the sensing time. If the sensing time is long, a time when motion of the user is limited may be increased. Thus, the bio-processor 130 according to an example embodiment of the inventive concepts may reduce (or, alternatively, minimize) a sensing time and may measure bioelectrical impedance based on the sensing voltage gathered during the reduced (or, alternatively, the minimized) sensing time. Herein, the bio-processor 130 may perform a processing operation of compensating a decrease in accuracy of a bioelectrical impedance value according to the reduced (or, alternatively, the minimized) sensing time. Such a processing time will be described in detail with reference to FIG. 2.

The bio-processor 130 may perform a function of measuring bioelectrical impedance and a function of generating bio-data, such as body fat data, depending on the bioelectrical impedance in an integrated manner. The bio-processor 130 may directly analyze bioelectrical impedance and may output the analyzed result to the application processor 140. In this case, compared with outputting data for bioelectrical impedance and user data to the application processor 140, an amount of data output from the bio-processor 130 may be reduced. Further, compared with analyzing bio-data based on bioelectrical impedance at a separate host device (not shown), an amount of data transmitted to the host device through the modem 190 may be reduced.

The application processor 140 may perform a control operation of controlling the bio-signal detecting system 100 and an arithmetic operation of calculating various data. The application processor 140 may execute an operating system (OS) and various applications. For example, the application processor 140 may provide query data for measuring, compensating, and analyzing bioelectrical impedance, and may provide user data for generating bio-data to the bio-processor 130. Herein, example embodiments are not limited thereto. For example, the bio-processor 130 may measure and compensate bioelectrical impedance. The application processor 140 may generate bio-data, such as body fat data, based on the compensated bioelectrical impedance.

The DDI 150 may receive image data based on bio-data analyzed by the bio-processor 130 or the application processor 140. For example, the application processor 140 may generate image data for displaying information associated with the analyzed bio-data. The DDI 150 may convert the image data into an image data voltage suitable for a specification of the display 160. The DDI 150 may output a gray scale voltage according to the image data as an image data voltage.

The display 160 may display information associated with bio-data. The display 160 may receive an image data voltage from the DDI and may display information associated with bio-data, such as body fat data, based on the image data voltage. The display 160 may include a liquid crystal display (LCD), an organic light emitting diode (OLED), an active matrix OLED (AMOLED), a flexible display, an electronic ink, or the like.

The storage device 170 may be used as an auxiliary memory of the application processor 140. Source codes of an OS or various applications executed by the application processor 140 and various data generated to be stored for a long time by the OS or the applications may be stored in the storage device 170. For example, execution codes for measuring or analyzing bioelectrical impedance, user data for calculating bio-data, or the like may be stored in the storage device 170. The storage device 170 may include a flash memory, a phase-change random access memory (PRAM), a magnetic RAM (MRAM), a ferroelectric RAM (FeRAM), a resistive RAM (RRAM), or the like.

The memory 180 may be used as a main memory of the application processor 140. For example, the memory 180 may store various data and process codes processed by the application processor 140. For example, measured bioelectrical impedance data, compensated bioelectrical impedance data, or bio-data may be stored in the memory 180. The memory 180 may include a dynamic RAM (DRAM), a static RAM (SRAM), a PRAM, an MRAM, an FeRAM, an RRAM, or the like.

The modem 190 may communicate with an external device, for example, a host device (not shown). For example, the modem 190 may transmit bio-data, received from the application processor 140, to the host device. The modem 190 may perform communication based on at least one of various wireless communication schemes, such as long term evolution (LTE), code division multiple access (CDMA), Bluetooth, near field communication (NFC), wireless-fidelity (Wi-Fi), and radio frequency identification (RFID), and various wired communication schemes, such as a universal serial bus (USB), serial AT attachment (SATA), a serial peripheral interface (SPI), an inter-integrated circuit (I2C), a high speed-I2C (HS-I2C), and an integrated-inter-chip sound (I2S).

Figure 2:
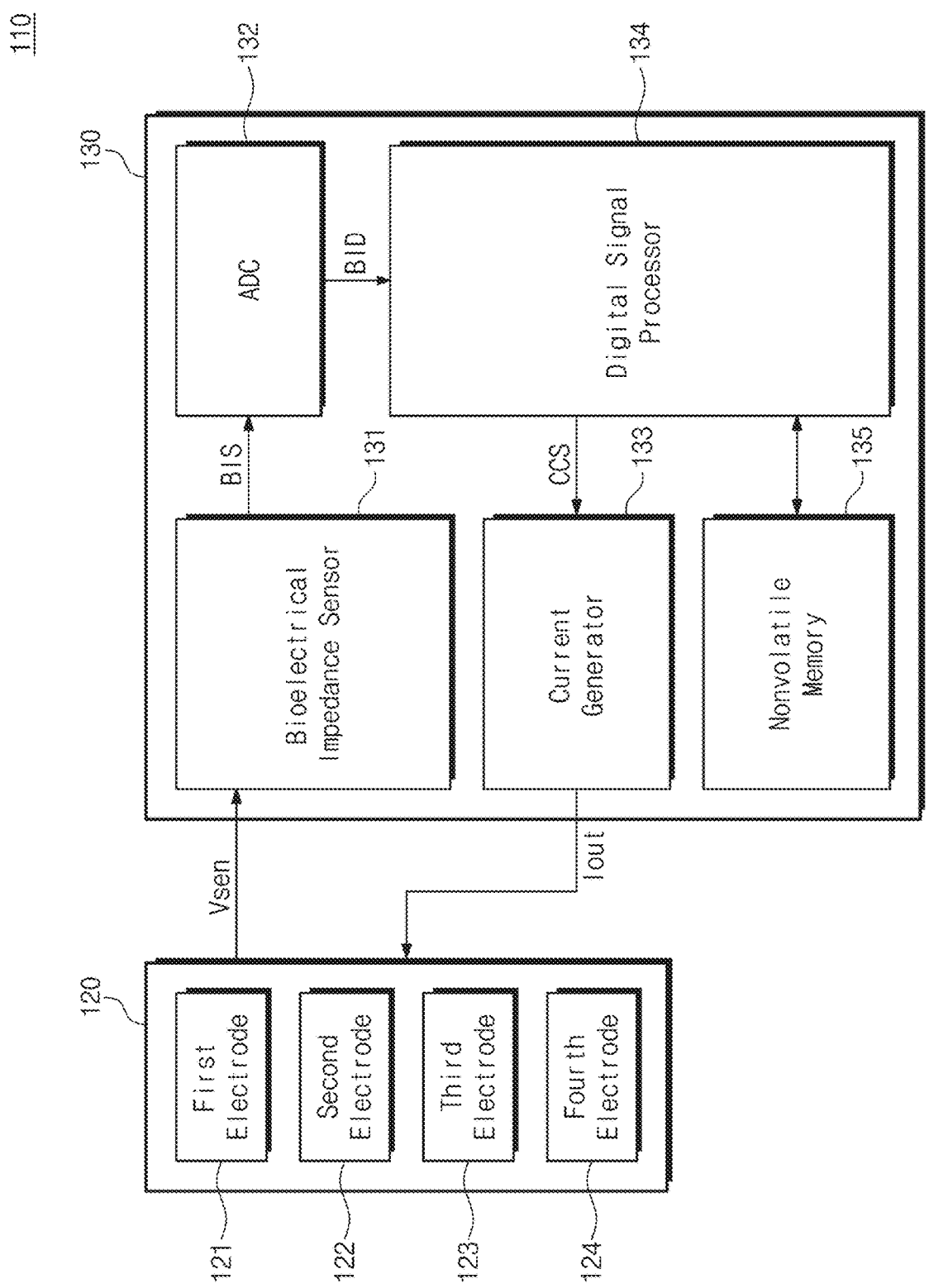
FIG. 2 is a block diagram illustrating an example configuration of a bio-signal detecting device of FIG. 1.

FIG. 2 is a block diagram illustrating an example configuration of a bio-signal detecting device of FIG. 1.

Referring to FIG. 2, a bio-signal detecting device 110 may include the electrode unit 120 and the bio-processor 130.

The electrode unit 120 may include electrodes. In FIG. 2, an example embodiment is illustrated in which the electrode unit 120 includes first to fourth electrodes 121 to 124. However, example embodiments are not limited thereto. For example, the electrode unit 120 may include various numbers of electrodes.

The bio-processor 130 may include a bioelectrical impedance sensor 131, an analog-digital converter (ADC) 132, a current generator 133, a digital signal processor 134, and a nonvolatile memory 135.

In some example embodiments, the bio-processor 130 may include processing circuitry and a memory (e.g., the nonvolatile memory 135), where the processing circuity is configured to perform the functions of one or more of the bioelectrical impedance sensor 131, the analog-digital converter (ADC) 132, the current generator 133, the digital signal processor 134. In other example embodiments, the bioelectrical impedance sensor 131, the analog-digital converter (ADC) 132, the current generator 133, the digital signal processor 134 may each include discrete processing circuity circuits.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

As discussed in more detail below, the processing circuity may be configured, through a layout design or execution of computer readable instructions stored in the memory (not shown), as a special purpose computer to measure a measured bioelectrical impedance during a sensing time such that the sensing time includes only a portion of a settling time prior to the measured bioelectrical impedance reaching a settled bioelectrical impedance value, estimate the settled bioelectrical impedance value based on changes in the measured bioelectrical impedance, and generate bio-data based on the settled bioelectrical impedance value. Therefore, the processing circuitry may improve the functioning of the bio-processor 130 itself by reducing an amount of time to generate the bio-data and increasing the accuracy of the generated bio-data.

The electrode unit 120 may receive an output current Iout from the current generator 133, and supply the output current Iout to a user. For example, the output current Iout may be supplied to the user through the second electrode 222 and the fourth electrode 224. The output current Iout may flow in a body of the user, and a potential difference by resistance of the body of the user may occur. The electrode unit 120 may receive a sensing voltage Vsen according to such a potential difference and may supply the received sensing voltage Vsen to the bio-processor 130. For example, the sensing voltage Vsen may be supplied to the bio-processor 130 through the first electrode 221 and the third electrode 223.

The first to fourth electrodes 221 to 224 may be configured to be in contact with the user when a bio-signal is measured. For example, the first electrode 221 and the second electrode 222 may be configured to be in contact with a left (or right) body of the user, and the third electrode 223 and the fourth electrode 224 may be configured to be in contact with a right (or left) body of the user. However, example embodiments are not limited thereto. The first electrode 221 and the second electrode 222 may be located to be adjacent to each other and may be insulated from each other. The third electrode 223 and the fourth electrode 224 may be located to be adjacent to each other and may be insulated from each other. The second electrode 222 and the fourth electrode 224 may form a closed circuit through the body of the user. The first electrode 221 adjacent to the second electrode 222 and the third electrode 223 adjacent to the fourth electrode 224 may supply a potential difference by the output current Tout which flows through the closed circuit, that is, the sensing voltage Vsen to the bioelectrical impedance sensor 131.

The bioelectrical impedance sensor 131 may measure bioelectrical impedance of the user based on the sensing voltage Vsen. The bioelectrical impedance sensor 131 may receive the sensing voltage Vsen from the electrode unit 120. The bioelectrical impedance sensor 131 may measure the bioelectrical impedance using the sensing voltage Vsen and the output current Tout. For this purpose, the bioelectrical impedance sensor 131 may include a voltmeter. The bioelectrical impedance sensor 131 may measure the bioelectrical impedance using a ratio of the sensing voltage Vsen to the output current Tout.

The bioelectrical impedance sensor 131 may generate a bioelectrical impedance signal BIS based on the measured bioelectrical impedance. For this purpose, the bioelectrical impedance sensor 131 may include an analog front end (AFE) (not shown). The AFE may include an amplifier (not shown) for amplifying the sensing voltage Vsen supplied from the first electrode 121 and the third electrode 123, that is, a potential difference between the first electrode 121 and the third electrode 123. The AFE may include a band filter for removing a noise of the amplified sensing voltage. A bandwidth of the band filter may be set based on a frequency of the output current Tout supplied from the current generator 133. The bioelectrical impedance sensor 131 may generate the bioelectrical impedance signal BIS by amplifying and filtering the sensing voltage Vsen.

The bioelectrical impedance sensor 131 may measure bioelectrical impedance during a sensing time that is set (or, alternatively, may be preset). The electrode unit 120 may be in contact with the user, and, when such a contact state is maintained, the sensing time when bioelectrical impedance is measured may be classified as including one or more of a floating time, a settling time, or a settled time. The floating time may be defined as a time before the user comes into contact with the electrode unit 120. The settling time may be defined as a time between a time when the user comes into contact with the electrode unit 120 and a time when bioelectrical impedance indicates a desired (or, alternatively, a predetermined) value. The settled time may be defined as a time when bioelectrical impedance indicates a desired (or, alternatively, a predetermined) value or a desired (or, alternatively, a predetermined) range. As discussed below, in one or more example embodiments, the sensing time may include a portion of the settling time.

The settling time may be determined according to various factors, for example, a size of each of the first to fourth electrodes 121 to 124, a shape of each of the first to fourth electrodes 121 to 124, an attitude of the user, or an internal characteristic of the user. If a bio-signal detecting system 100 of FIG. 1 is implemented as a small wearable device, each of the first to fourth electrodes 121 to 124 may be small in size. As each of the first to fourth electrodes 121 to 124 decreases in size, a settling time may increase.

The bioelectrical impedance sensor 131 may measure a bioelectrical impedance signal during a portion of a settling time without also measuring the bioelectrical impedance during the settled time. As will be described below, since the bio-processor 130 estimates settled bioelectrical impedance based on measured bioelectrical impedance without waiting until the settled time, the bio-processor 130 may quickly generate bio-data. A description will be given of detailed contents with reference to FIG. 3.

The ADC 132 may convert the bioelectrical impedance signal BIS into bioelectrical impedance data BID. The ADC 132 may receive the bioelectrical impedance signal BIS which is an analog signal from the bioelectrical impedance sensor 131. The ADC 132 may convert the bioelectrical impedance signal BIS into the bioelectrical impedance data BID which is a digital signal and may output the converted bioelectrical impedance data BID to the digital signal processor 134.

The current generator 133 may generate the output current Iout for measuring bioelectrical impedance. The current generator 133 may supply the output current Iout to the electrode unit 120. The current generator 133 may supply the output current Iout to the electrode unit 120 under control of the digital signal processor 134. The current generator 133 may generate the output current Iout based on a current control signal CCS provided from the digital signal processor 134. The output current Iout may be an alternating current (AC) having a level which is harmless to humans. For example, the output current Iout may be, but is not limited to, a microcurrent having a frequency of 50 KHz.

The digital signal processor 134 may estimate a settled bioelectrical impedance value based on measured bioelectrical impedance. The digital signal processor 134 may receive the bioelectrical impedance data BID from the ADC 132. The bioelectrical impedance data BID may be generated based on bioelectrical impedance measured during a sensing time that is set relatively short without waiting for the settling time. Therefore, if the settling time is too long such that the sensing time does not include the settled time, the bioelectrical impedance data BID may only include information measured during a portion of the settling time and fail to include information about bioelectrical impedance measured during the settled time.

The digital signal processor 134 may analyze a pattern of bioelectrical impedance during a sensing time and may estimate a settled bioelectrical impedance value. The digital signal processor 134 may model changes over a time of measured bioelectrical impedance as a fitting function. For example, the fitting function may be, but is not limited to, a natural logarithmic function. For example, the fitting function may include various functions such as an exponential function. The digital signal processor 134 may determine a coefficient or a constant of the fitting function based on changes in measured bioelectrical impedance. The digital signal processor 134 may determine a settled time of bioelectrical impedance based on the determined coefficient or constant of the fitting function. The digital signal processor 134 may estimate a settled bioelectrical impedance value at the determined settled time.

The digital signal processor 134 may compare a modeled fitting function with a pattern of measured bioelectrical impedance to determine a contact error. If a contact state between the user and the electrode unit 120 is poor, a real waveform of bioelectrical impedance may be indicated in an unsettled manner. In other words, a difference between a waveform of measured bioelectrical impedance and a modeled fitting function may be greatly indicated. If a result of accumulating a difference between the modeled fitting function and the measured bioelectrical impedance is greater than an error reference value, the digital signal processor 134 may determine that a contact error occurs. In this case, the digital signal processor 134 may control the bio-processor 130 to re-measure bioelectrical impedance.

The digital signal processor 134 may generate bio-data using the settled bioelectrical impedance value. For example, the digital signal processor 134 may apply the settled bioelectrical impedance value to regression data. The regression data may include desired (or, alternatively, predetermined) function information to calculate body fat of the user. The digital signal processor 134 may generate the bio-data based on a parameter and the settled bioelectrical impedance value. For example, the parameter may further include information about a height, a weight, an age, or a gender of the user. The digital signal processor 134 may generate bio-data by receiving regression data and user information from the nonvolatile memory 135.

The nonvolatile memory 135 may store various data for analyzing bioelectrical impedance and generating bio-data. For example, fitting function data for estimating a settled bioelectrical impedance value may be stored in the nonvolatile memory 135. Further, user information and regression data for generating bio-data using an estimated bioelectrical impedance value may be stored in the nonvolatile memory 135. The nonvolatile memory 135 may be, but is not limited to, a NAND flash memory. For example, the nonvolatile memory 135 may be a NOR flash memory, a PRAM, an MRAM, an RRAM, an FeRAM, or an electrically erasable and programmable read only memory (EEPROM).

Figure 3:
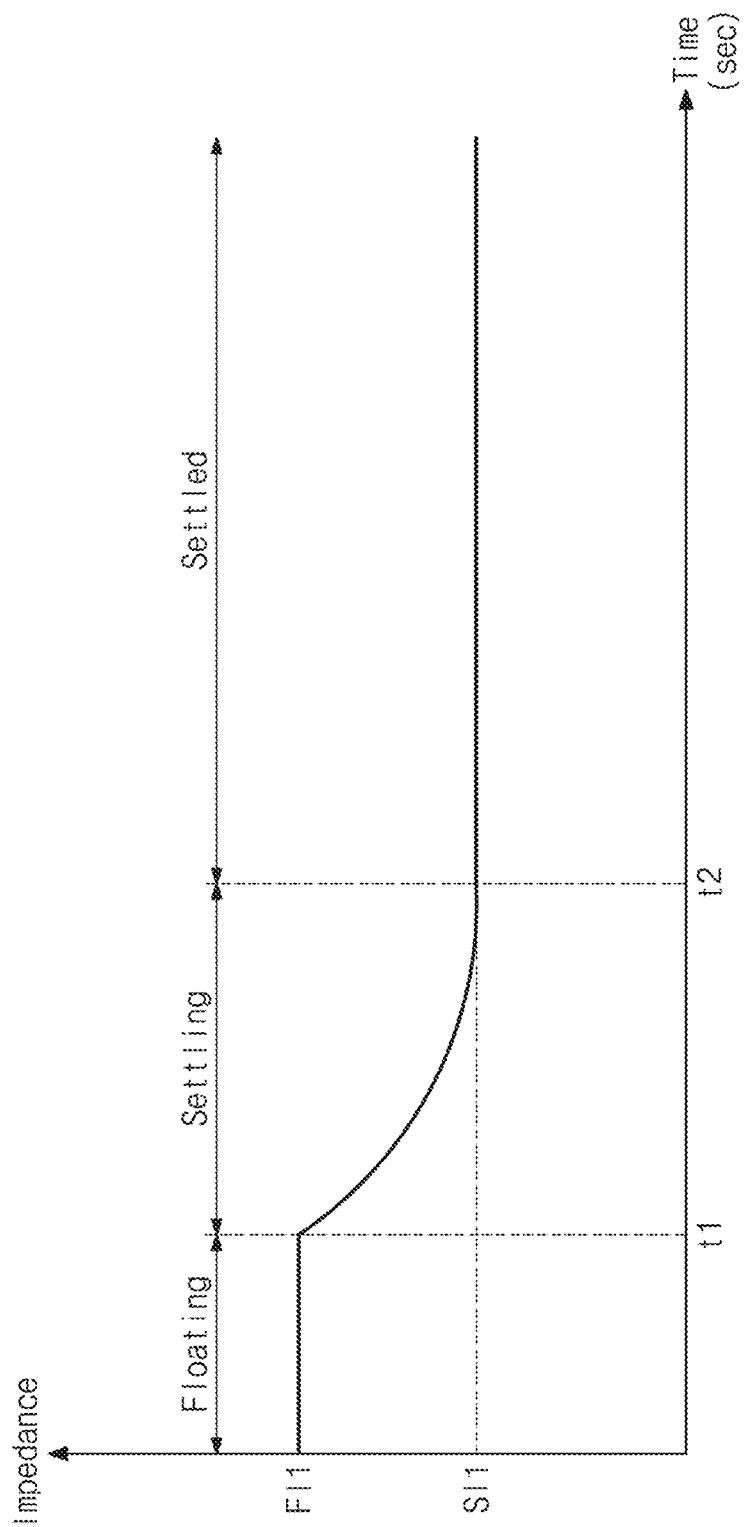
FIG. 3 is a graph illustrating changes in bioelectrical impedance measured over time.

FIG. 3 is a graph illustrating changes in bioelectrical impedance measured over time.

Referring to FIG. 3, a horizontal axis may represent the flow of time, and a vertical axis may represent bioelectrical impedance. A bioelectrical impedance value may be indicated by being classified as a floating time, a settling time, or a settled time. For convenience of description, a description will be given of FIG. 3 with reference to reference numerals of FIGS. 1 and 2.

The floating time may be defined as a time before a first time point t1. The floating time may indicate a time before a user comes into contact with an electrode unit 120. In other words, the first time point t1 may represent a time when the user starts to be in contact with the electrode unit 120. The user may fail to come into contact with the electronic device 120 during the floating time. Thus, a closed circuit may fail to be formed between the user and the electrode unit 120. During the floating time, bioelectrical impedance measured from a bioelectrical impedance sensor 131 may have a floating impedance value FI1.

The settling time may be defined as a time between the first time point t1 and a second time point t2. The settling time may indicate a time before bioelectrical impedance is settled after the user comes into contact with the electrode unit 120. In other words, the second time point t2 may indicate a time when bioelectrical impedance is settled. During the settling time, a closed circuit may be formed between the user and the electrode unit 120. Thus, the bioelectrical impedance sensor 131 may have an impedance value lower than the floating impedance value FI1. Bioelectrical impedance may be gradually reduced during the settling time, and it may have a settled bioelectrical impedance value SI1 at the second time point t2.

The settled time may be defined as a time after the second time point t2. The settled time may represent a time which is in a settled state, after the settling time passes after the user and the electrode unit 120 are in contact with each other. During the settled time, the closed circuit formed between the user and the electrode unit 120 may be kept. If the bioelectrical impedance sensor 131 measures bioelectrical impedance during the settled time, the measured bioelectrical impedance may have the settled bioelectrical impedance value SI1. In FIG. 3, an example embodiment is illustrated in which the settled bioelectrical impedance value SI1 is kept constant. However, example embodiments are not limited thereto. For example, during the settled time, bioelectrical impedance may be formed within a specific range with respect to the settled bioelectrical impedance value SI1.

It may be preferable that the settled bioelectrical impedance value SI1 is used to generate bio-data associated with body composition of the user. Herein, the settled bioelectrical impedance value SI1 may be detected after the second time point t2. In general, if the user remains in contact with the electrode unit 120 during at least the entire duration of the settling time between the first time point t1 and the second time point t2, a bio-processor 130 may generate settled bio-data. Herein, if a bio-signal detecting system 100 is implemented with a small size, the electrode unit 120 may be reduced in size and thus the settling time may be increased. As a contact time between the user and the electrode unit 120 is longer, the user may feel more uncomfortable. There may be a high probability that the user does not come into contact with the electrode unit 120 for the full settling time.

Figure 4:
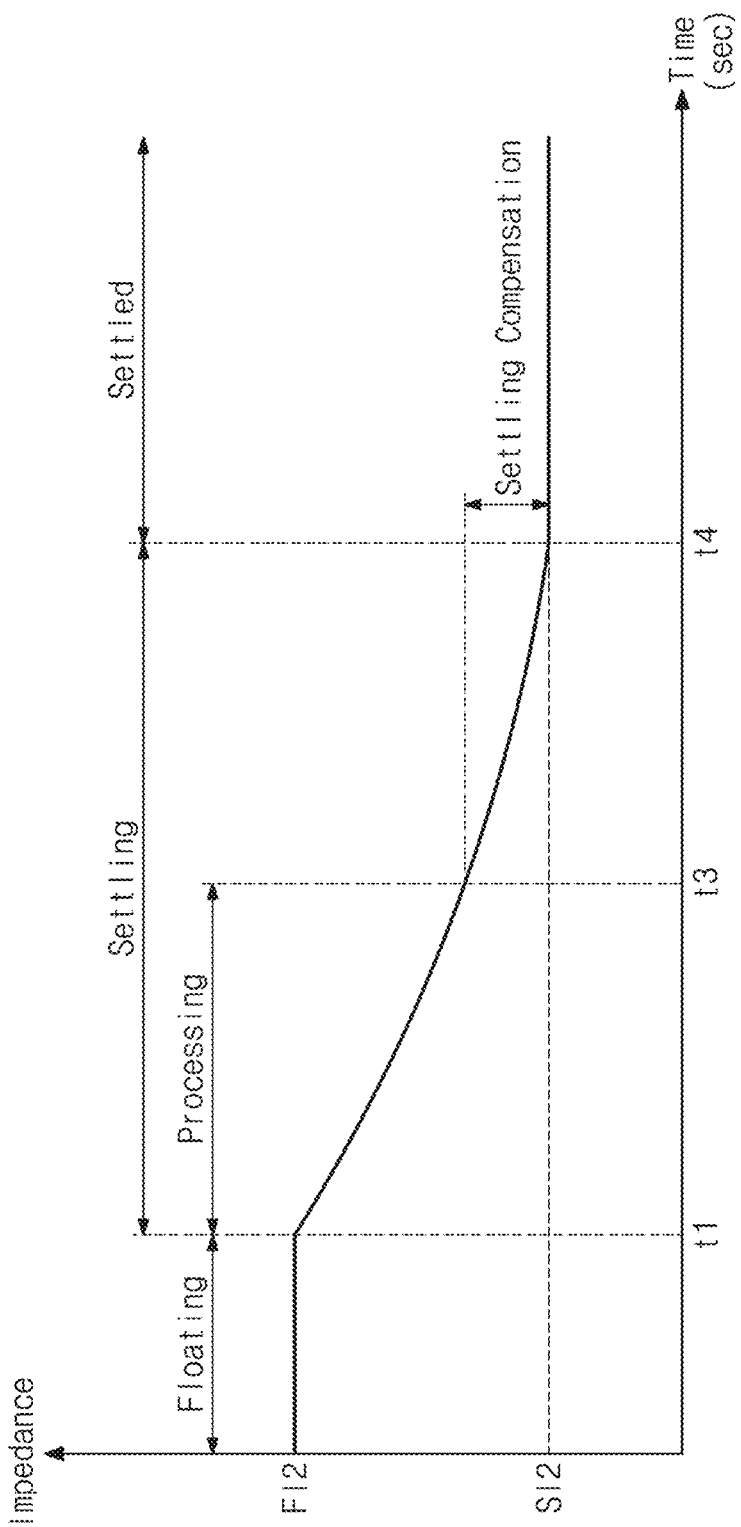
FIGS. 4 and 5 are graphs illustrating a process of measuring bioelectrical impedance and estimating a settled bioelectrical impedance value at a bio-processor of FIG. 2.
Figure 5:
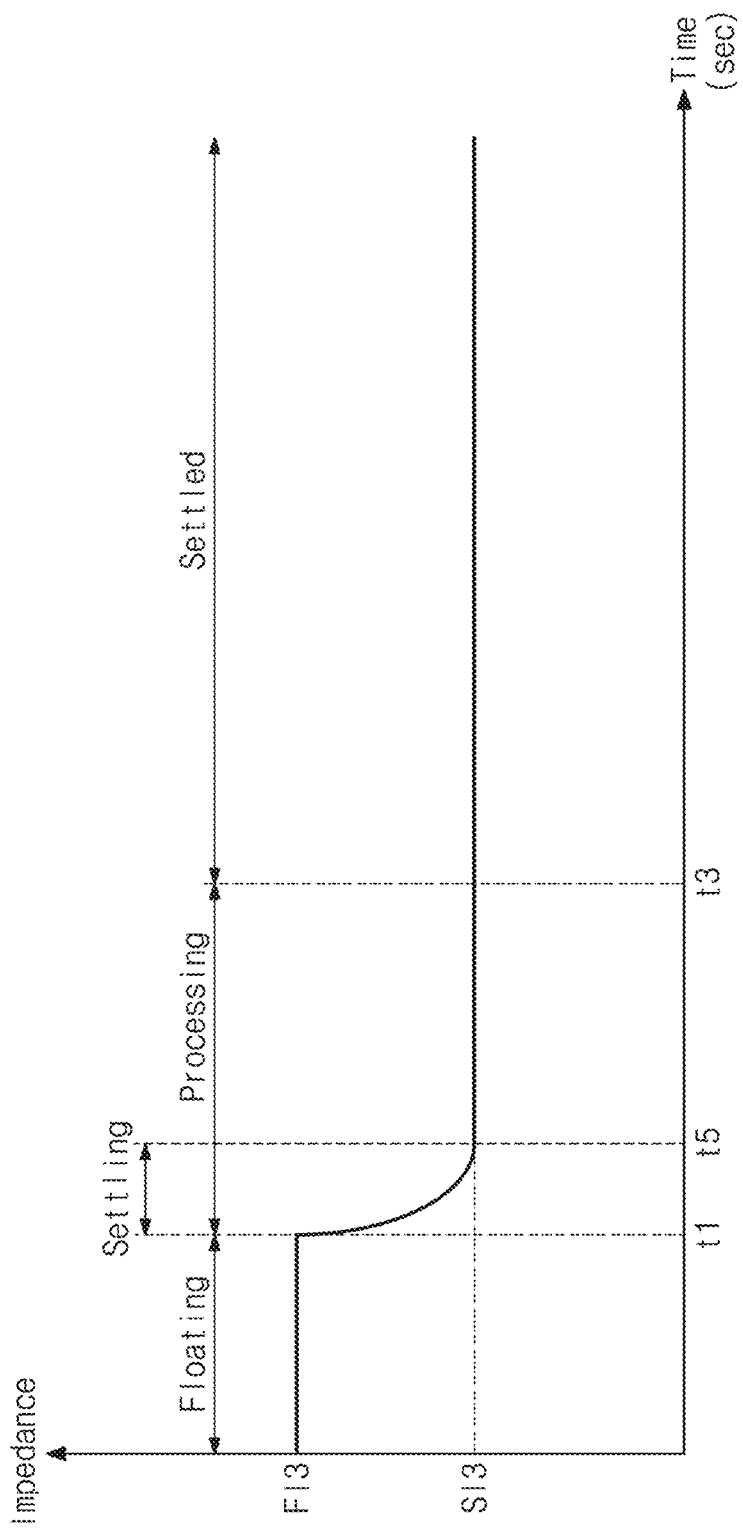

FIGS. 4 and 5 are graphs illustrating a process of measuring bioelectrical impedance and estimating a settled bioelectrical impedance value at a bio-processor of FIG. 2. Referring to FIGS. 4 and 5, a horizontal axis may represent the flow of time, and a vertical axis may represent bioelectrical impedance. A bioelectrical impedance value may be indicated by being classified as a floating time, a settling time, or a settled time. For convenience of description, a description will be given of FIGS. 4 and 5 with reference to reference numerals of FIGS. 1 and 2.

FIG. 4 is a drawing illustrating a method for estimating a settled bioelectrical impedance value when a bioelectrical impedance value is measured during a processing time which is shorter than a settling time.

Referring to FIG. 4, a floating time may be defined as a time before a first time point t1. In the floating time, bioelectrical impedance may have a floating impedance value FI2. A processing time may be defined as a time between the first time point t1 and a third time point t3. A settling time may be defined as a time between the first time point t1 and a fourth time point t4 which is later than a third time t3. A settled time may be after the fourth time point t4. In the settled time, bioelectrical impedance may have a settled bioelectrical impedance value SI2.

The processing time may be a sensing time described with reference to FIG. 2. In other words, the processing time may be a time when a bioelectrical impedance sensor 131 receives a sensing voltage Vsen and measures bioelectrical impedance. Herein, example embodiments are not limited thereto. For example, the processing time may be a time to estimate a settled bioelectrical impedance value by a bio-processor 130 in a time when the bio-processor 130 measures bioelectrical impedance. The processing time may be shorter than the settling time. Contrary to being shown in FIG. 4, a start point of the processing time may be a time after the first time point t1. During the processing time, measured bioelectrical impedance may be reduced over time. Herein, since the processing time is shorter than the settling time, a bioelectrical impedance value at the third time point t3 may be different from (e.g., larger than) the settled bioelectrical impedance value SI2.

The bio-processor 130 may model changes in bioelectrical impedance between the first time point t1 and the third time point t3 as a fitting function. For example, a fitting function f(t) may be defined as a natural logarithmic function "A*ln(t)+B". The bio-processor 130 may calculate an A value and a B value corresponding to the nearest fitting function to bioelectrical impedance measured during the processing time. For example, the bio-processor 130 may extract an A value and a B value in which a difference between a measured bioelectrical impedance value and a fitting function is minimized with respect to time. As the settling time is longer, an absolute value of A may be more reduced. Further, as the settled bioelectrical impedance value SI2 is larger, the B value may be larger.

The bio-processor 130 may estimate the settled bioelectrical impedance value SI2 based on a determined fitting function. For example, the bio-processor 130 may estimate the value of the bioelectrical impedance at the fourth time point t4 based on the determined fitting function. The bio-processor 130 may compensate the settled bioelectrical impedance value SI2 using a value of a fitting function for the fourth time point t4. The bio-processor 130 may accumulate and calculate a difference between a measured bioelectrical impedance value and a fitting function to ensure reliability of the fitting function. If the accumulated and calculated result is greater than an error reference value, the bio-processor 130 may determine that there is no reliability of measured bioelectrical impedance. In other words, the bio-processor 130 may determine that a contact error with a user or the like occurs and may re-measure bioelectrical impedance.

Since the bio-processor 130 measures bioelectrical impedance for a portion of the settling time and determines the bioelectrical impedance value SI2, a measurement time of the user may be reduced. In other words, the bio-processor 130 according to an example embodiment may not wait to measure bioelectrical impedance until the settled time. Further, since a contact error is determined using an accumulated and calculated error value of bioelectrical impedance for a portion of the settling time, bioelectrical impedance may be measured again before the fourth time point t4 and reliability of the settled bioelectrical impedance value SI2 may increase.

FIG. 5 is a drawing illustrating a method for estimating a settled bioelectrical impedance value when bioelectrical impedance is measured during a processing time which is longer than a settling time.

Referring to FIG. 5, a floating time may be defined as a time before a first time point t1. In the floating time, bioelectrical impedance may have a floating impedance value FI3. A processing time may be defined as a time between the first time point t1 and a third time point t3. A settling time may be defined as a time between the first time point t1 and a fifth time point t5 which is earlier than a third time point t3. A settled time may be defined as being after the third time point t3. In the settled time, bioelectrical impedance may have a settled bioelectrical impedance value SI3.

The processing time may be a sensing time described with reference to FIG. 2. Alternatively, the processing time may be a time to estimate a settled bioelectrical impedance value by the bio-processor 130. The processing time may be longer than the settling time. Contrary to being shown in FIG. 5, a start point of the processing time may be a time after the first time point t1. In a time between the first time point t1 and the fifth time point t5 in the processing time, measured bioelectrical impedance may be reduced over time. In a time between the fifth time point t5 and the third time point t3 in the processing time, the measured bioelectrical impedance may arrive at a settled state and may indicate the settled bioelectrical impedance value S13.

To ensure user convenience, it may be preferable that the bio-processor 130 has a processing time which is shorter than a settling time and estimates a settled bioelectrical impedance value before arriving at a settled time. The bio-processor 130 may set a processing time or a sensing time which is shorter than a settling time with respect to an average settling time of a general user. Herein, according to an internal characteristic of the user or the like, as shown in FIG. 5, the processing time may be longer than the settling time.

The bio-processor 130 may model changes in bioelectrical impedance between the first time point t1 and the third time point t3 as a fitting function. For example, the fitting function may be a natural logarithmic function. As shown in FIG. 4, the bio-processor 130 may estimate the settled bioelectrical impedance value S13 based on a modeled fitting function. The bio-processor 130 may determine whether the settling time is shorter than the processing time and if the settled bioelectrical impedance value S13 is maintained longer than a specified reference time, the bio-processor 130 may immediately determine the settled bioelectrical impedance value S13 without modeling changes in bioelectrical impedance.

Figure 6:
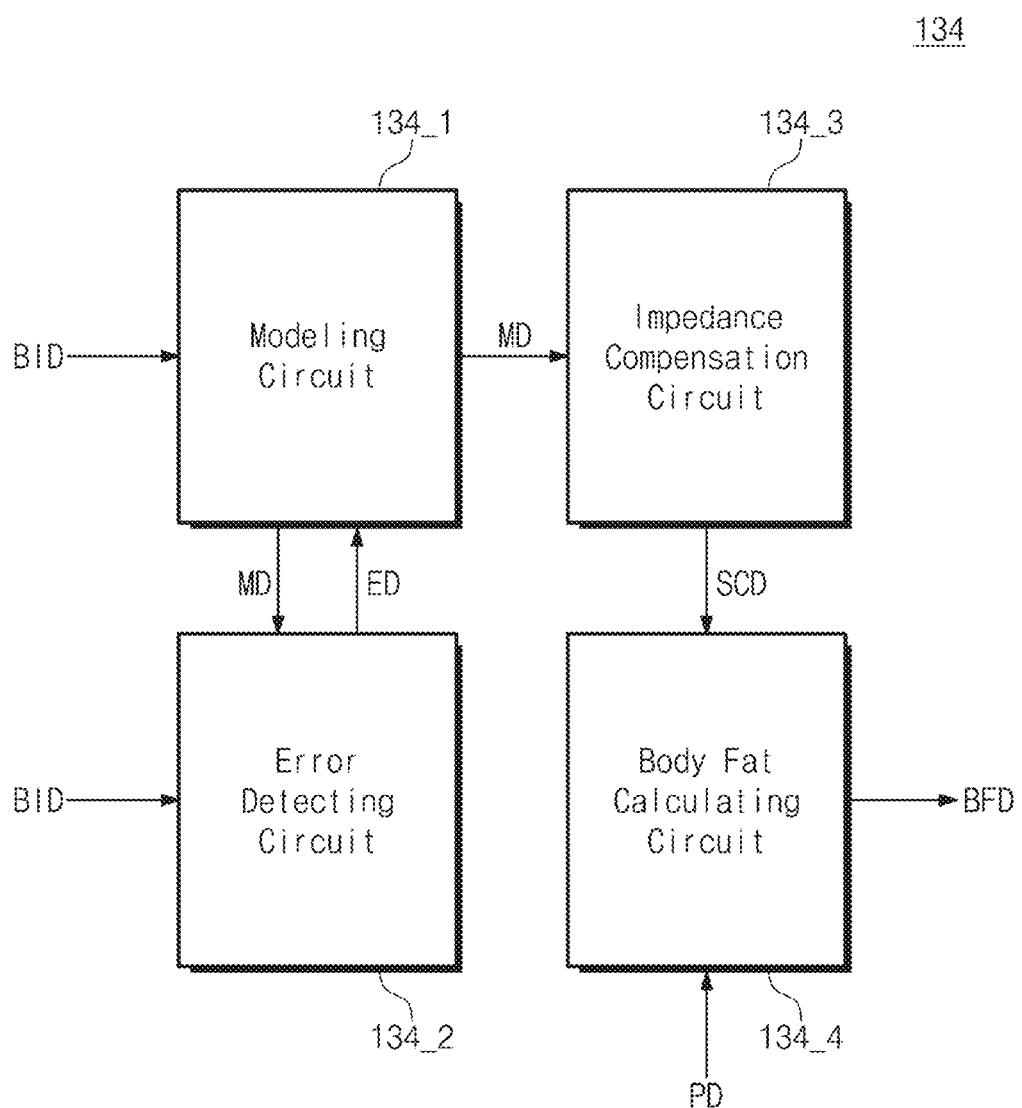
FIG. 6 is a block diagram illustrating an example configuration of a digital signal processor of FIG. 2.

FIG. 6 is a block diagram illustrating an example configuration of a digital signal processor of FIG. 2.

Referring to FIG. 6, a digital signal processor 134 may generate bio-data including body fat data BFD. The digital signal processor 134 may generate bio-data in various manners and is not limited to an embodiment of FIG. 6.

The digital signal processor 134 may be configured, through a layout design or execution of computer readable instructions stored in the memory (not shown), as a special purpose computer to perform the functions of one or more of a modeling circuit 134_1, an error detecting circuit 134_2, an impedance compensation circuit 134_3, and a body fat calculating circuit 134_4. For convenience of description, a description will be given of FIG. 6 with reference numerals of FIG. 2.

The modeling circuit 134_1 may model bioelectrical impedance measured during a sensing time or a processing time as a fitting function. The modeling circuit 134_1 may receive bioelectrical impedance data BID from an ADC 132. The modeling circuit 134_1 may determine a coefficient or a constant of the fitting function based on the bioelectrical impedance data BID. For example, the modeling circuit 134_1 may determine a fitting function as a natural logarithmic function and may determine a coefficient value and a constant value of the nearest natural logarithmic function to changes in a value of the bioelectrical impedance data BID over time. The modeling circuit 134_1 may generate modeling data MD based on the determined coefficient value and the determined constant value.

The error detecting circuit 132_2 may compare the modeled fitting function with actually measured bioelectrical impedance to determine a contact error by an attitude of a user. The error detecting circuit 134_2 may receive the modeling data MD from the modeling circuit 134_1. The error detecting circuit 134_2 may receive the bioelectrical impedance data BID from the ADC 132. The error detecting circuit 134_2 may compare the modeling data MD with the bioelectrical impedance data BID. The error detecting circuit 134_2 may accumulate and calculate a difference value between the modeling data MD and the bioelectrical impedance data BID. If the accumulated and calculated result is greater than an error reference value, the error detecting circuit 134_2 may determine that a contact error occurs and may generate error data ED.

Based on the error data ED, the digital signal processor 134 may fail to estimate settled bioelectrical impedance. The error detecting circuit 134_2 may provide the error data ED to the modeling circuit 134_1. When receiving the error data ED, the modeling circuit 134_1 may fail to provide the modeling data MD to the impedance compensation circuit 134_3. In this case, the digital signal processor 134 may control a bio-processor 130 to measure bioelectrical impedance again without calculating settled bioelectrical impedance. Contrary to being shown in FIG. 6, the error data ED is provided to the impedance compensation circuit 134_3 to stop calculating settled bioelectrical impedance, or the error data ED is provided to the body fat calculating circuit 134_4 to stop calculating body fat data BFD.

The impedance compensation circuit 134_3 may estimate a settled bioelectrical impedance value based on the modeled fitting function. The impedance compensation circuit 134_3 may receive the modeling data MD from the modeling circuit 134_1. The impedance compensation circuit 134_3 may determine a settled time of bioelectrical impedance from the modeling data MD, and an estimated value of the bioelectrical impedance at the settled time. For example, the impedance compensation circuit 134_3 may predict a waveform according to a coefficient value and a constant value of a fitting function and may estimate a settled time of bioelectrical impedance depending on the predicted waveform. The impedance compensation circuit 134_3 may calculate a value of the fitting function at the settled time to generate settled bioelectrical impedance data SCD.

The body fat calculating circuit 134_4 may calculate body fat of the user based on the estimated bioelectrical impedance value. The body fat calculating circuit 134_4 may receive the settled bioelectrical impedance data SCD from the impedance compensation circuit 134_3. The body fat calculating circuit 134_4 may receive user data PD from the nonvolatile memory 135 or the application processor 140 (see FIGS. 1 and 2). The user data PD may include information associated with the user. For example, the user data PD may include information indicating a height, a weight, an age, and/or a gender of a user. However, example embodiments are not limited thereto. The body fat calculating circuit 134_4 may apply the user data PD and the settled bioelectrical impedance data SCD as parameters to a regression equation. The body fat calculating circuit 134_4 may additionally receive data for such a regression equation from the nonvolatile memory 135.

The body fat calculating circuit 134_4 may generate body fat data BFD by applying various parameters including the settled bioelectrical impedance data SCD to the regression equation. The body fat data BFD may be output according to a request of the application processor 140 and/or an external host device. In this case, compared with directly processing the bioelectrical impedance data BID and calculating body fat data BFD at the application processor 140 or the external host device, by calculating the body fat data BFD at the bio processor 130 an amount of transmitted data may be reduced and power consumption according to data transmission may be reduced.

Figure 7:
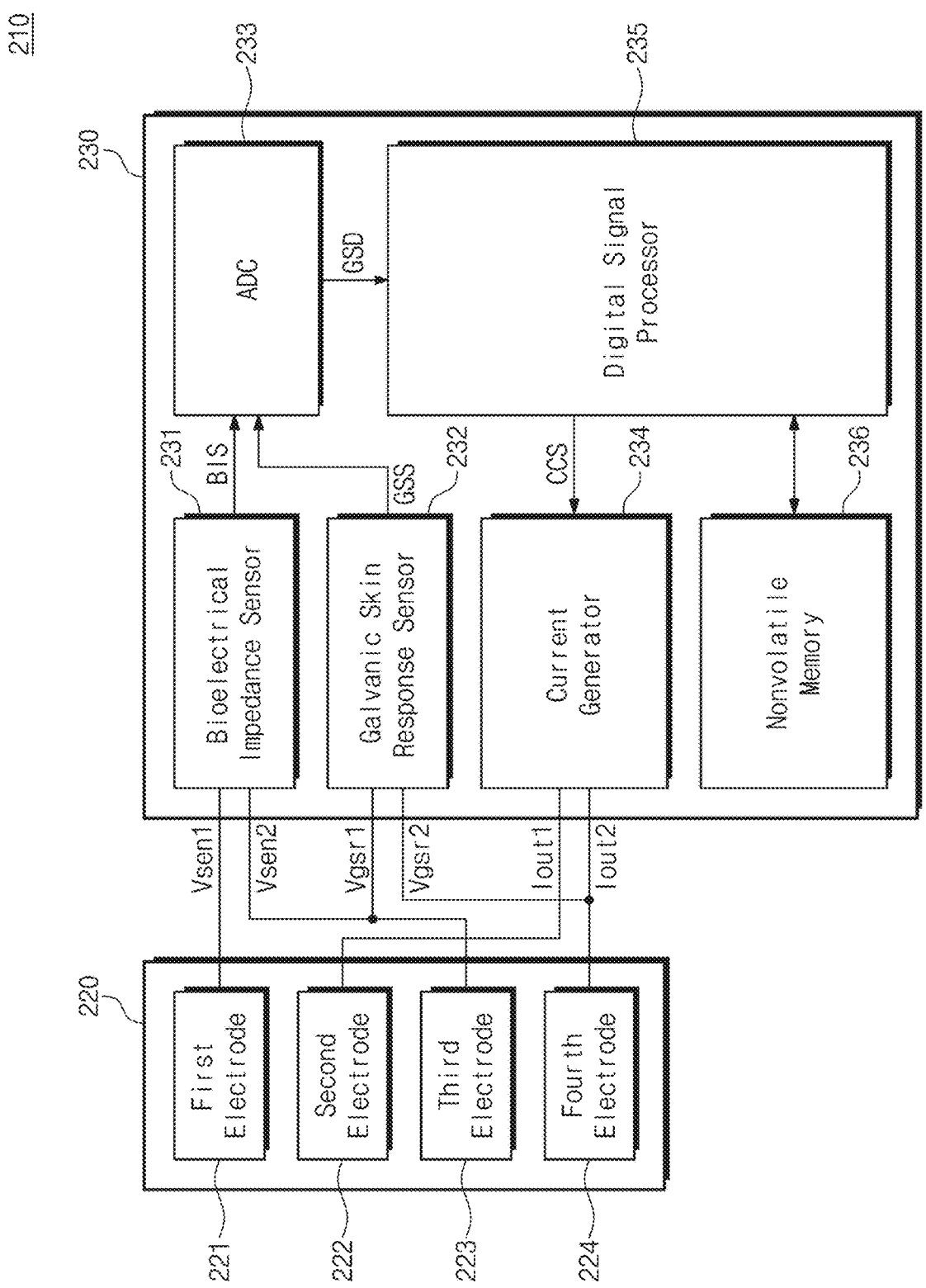
FIG. 7 is a block diagram illustrating another example configuration of a bio-signal detecting device of FIG. 1.

FIG. 7 is a block diagram illustrating another example configuration of a bio-signal detecting device of FIG. 1. A bio-signal detecting device 210 may be a bio-signal detecting device 110 of FIG. 1.

Referring to FIG. 7, the bio-signal detecting device 210 may include an electrode unit 220 and a bio-processor 230.

The bio-processor 230 may include a bioelectrical impedance sensor 231, a Galvanic skin response sensor 232, an ADC 233, a current generator 234, a digital signal processor 235, and a nonvolatile memory 236.

The electrode unit 220 may include first to fourth electrodes 221 to 224. The electrode unit 220 may supply a first output current Iout1 and a second output current Iout2, received from the current generator 234, to a user. The second electrode 222 may supply the first output current Iout1 to the user, and the fourth electrode 224 may supply the second output current Iout2 to the user. As the electrode unit 220 supplies the first output current Iout1 and the second output current Iout2 to the user, it may receive a generated first sensing voltage Vsen1 and a generated second sensing voltage Vsen2 and may supply the first sensing voltage Vsen1 and the second sensing voltage Vsen2 to the bioelectrical impedance sensor 231. The first electrode 221 may supply the first sensing voltage Vsen1 to the bioelectrical impedance sensor 231, and the third electrode 223 may supply the second sensing voltage Vsen2 to the bioelectrical impedance sensor 231. The process of supplying an output current to the user to measure bioelectrical impedance and supplying a sensing voltage to the bio-processor 230 at the first to fourth electrodes 221 to 224 may be the same as that in FIG. 2.

The electrode unit 220 may receive a first Galvanic voltage Vgsr1 and a second Galvanic voltage Vgsr2 and may supply the first Galvanic voltage Vgsr1 and the second Galvanic voltage Vgsr2 to the Galvanic skin response sensor 232 to measure electric skin resistance by a Galvanic skin response. An operation of the electrode unit 220 for measuring bioelectrical impedance and an operation of the electrode unit 220 for measuring electric skin resistance by a Galvanic skin response may be generated in a different time. To measure electric skin resistance, it may be assumed that the third electrode 223 and the fourth electrode 224 are used. The third electrode 223 and the fourth electrode 224 may be located to be adjacent to each other and may be insulated from each other.

The third electrode 223 and the fourth electrode 224 may receive a direct current (DC) from the current generator 234 and may supply the received DC to the user. In this case, resistance between the third electrode 223 and the fourth electrode 224 through the user may be changed by a Galvanic skin response. The Galvanic skin response may be indicated based on states of sweat glands. A potential difference may be formed between the third electrode 223 and the fourth electrode 224 based on the changed resistance. The third electrode 223 may receive the first Galvanic voltage Vgsr1 and may supply the first Galvanic voltage Vgsr1 to the Galvanic skin response sensor 232, and the fourth electrode 224 may receive the second Galvanic voltage Vgsr2 and may supply the second Galvanic voltage Vgsr2 to the Galvanic skin response sensor 232.

The bioelectrical impedance sensor 231 may measure bioelectrical impedance of the user based on the first sensing voltage Vsen1 and the second sensing voltage Vsen2. The bioelectrical impedance sensor 231 may generate a bioelectrical impedance signal BIS based on the measured bioelectrical impedance. Since a configuration and function of the bioelectrical impedance sensor 231 is the same as that of a bioelectrical impedance sensor 131 of FIG. 2, a detailed description will be omitted.

The Galvanic skin response sensor 232 may measure electric skin resistance of the user based on the first Galvanic voltage Vgsr1 and the second Galvanic voltage Vgsr2. The Galvanic skin response sensor 232 may sense changes in resistance using the first Galvanic voltage Vgsr1 and the second Galvanic voltage Vgsr2. For this purpose, the Galvanic skin response sensor 232 may include a voltmeter. The Galvanic skin response sensor 232 may measure changes in resistance according to a change in the first Galvanic voltage Vgsr1 and the second Galvanic voltage Vgsr2.

The Galvanic skin response sensor 232 may generate a Galvanic skin response signal GSS based on the measured electric skin resistance. For this purpose, the Galvanic skin response sensor 232 may include an AFE (not shown). The AFE may include an amplifier (not shown) for amplifying a potential difference between the first Galvanic voltage Vgsr1 and the second Galvanic voltage Vgsr2. The AFE may include a low pass filter (LPF) for removing a noise of an amplified Galvanic voltage.

The Galvanic skin response sensor 232 may measure electric skin resistance before a sensing time for measuring bioelectrical impedance. In other words, after the Galvanic skin response sensor 232 measures the electric skin resistance, the bioelectrical impedance sensor 231 may measure bioelectrical impedance. In FIG. 7, an example embodiment illustrates that the Galvanic skin response sensor 232 and the bioelectrical impedance sensor 231 are independent of each other. However, example embodiments are not limited thereto. For example, the Galvanic skin response sensor 232 and the bioelectrical impedance sensor 231 may be integrated into one configuration.

The ADC 233 may convert the bioelectrical impedance signal BIS into bioelectrical impedance data BID. The ADC 233 may convert the Galvanic skin response signal GSS into Galvanic skin response data GSD. Since a configuration and function of the ADC 233 is the same as that of an ADC 132 of FIG. 2, a detailed description will be omitted.

The current generator 234 may generate the first output current Iout1 and the second output current Iout2 for measuring bioelectrical impedance. The current generator 234 may supply the first output current Iout1 to the second electrode 222 and may supply the second output current Iout2 to the fourth electrode 224. The current generator 234 may generate a DC for measuring electric skin resistance. The current generator 234 may supply the DC to the third electrode 223 or the fourth electrode 224. The current generator 234 may generate the first and second output currents Iout1 and Iout2 or may generate the DC, based on a current control signal CSS.

The digital signal processor 235 may estimate a settled bioelectrical impedance value based on measured bioelectrical impedance. Since a process of estimating the settled bioelectrical impedance value is the same as that described with reference to FIG. 2, a detailed description will be omitted. The digital signal processor 235 may compensate a settled bioelectrical impedance value based on additionally measured electric skin resistance. For example, the digital signal processor 235 may estimate a contact resistance value at a time where bioelectrical impedance is settled, based on the measured electric skin resistance. Herein, contact resistance may refer to resistance by a contact between a user and the electrode unit 220, in which a degree of skin dryness by sweat or the like is reflected. The digital signal processor 235 may use a contact resistance value as a parameter of regression data to compensate the contact resistance value for an estimated bioelectrical impedance value.

The digital signal processor 235 may predict a settling time of bioelectrical impedance based on measured electric skin resistance and measured bioelectrical impedance. The digital signal processor 235 may analyze a pattern of bioelectrical impedance measured during a sensing time and may model the analyzed pattern as a fitting function. The digital signal processor 235 may reflect electric skin resistance measured in the process of modeling the fitting function. In other words, the digital signal processor 235 may determine a coefficient and a constant of the fitting function based on measured electric skin resistance and measured bioelectrical impedance. Herein, example embodiments are not limited thereto. For example, the digital signal processor 235 may model a fitting function based on measured bioelectrical impedance and may predict a settling time to estimate a settled bioelectrical impedance value, thus reflecting measured electric skin resistance to compensate a bioelectrical impedance value.

The digital signal processor 235 may predict a contact time between the electrode unit 220 and the user based on measured electric skin resistance. For example, if a biosignal detecting system 100 is implemented as a wearable device, the wearable device may have already been already worn prior to the present iteration of measuring the bioelectrical impedance. The digital signal processor 235 may predict a time when the wearable device is worn, depending on states of sweat glands of the user based on measured electric skin resistance. The digital signal processor 235 may model electric skin resistance according to the time when the wearable device is worn and may predict a contact resistance value at a time when bioelectrical impedance is settled. The digital signal processor 235 may compensate a settled bioelectrical impedance value by reflecting the predicted contact resistance value.

Figure 8:
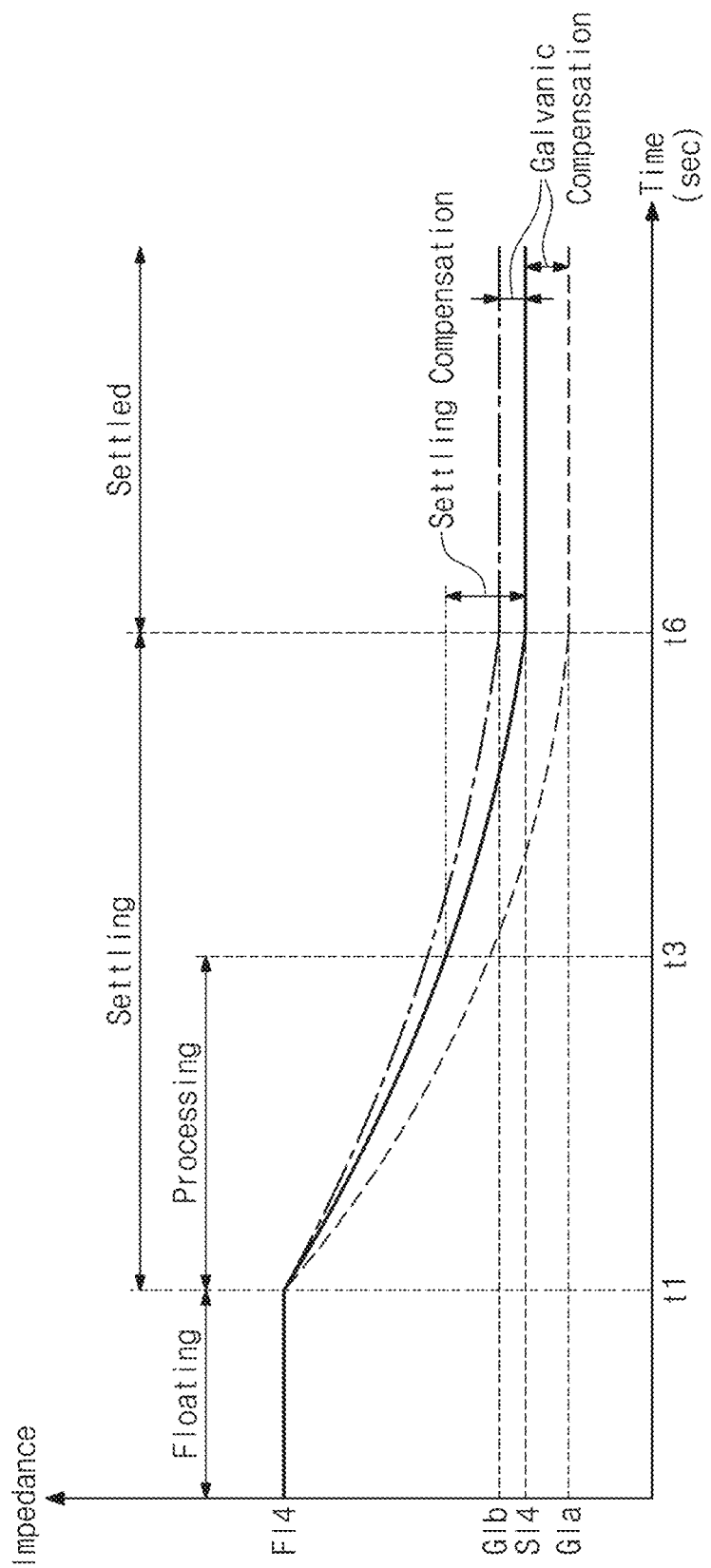
FIG. 8 is a graph illustrating a process of estimating a settled bioelectrical impedance value depending on bioelectrical impedance and electric skin resistance at a bio-processor of FIG. 7.

FIG. 8 is a graph illustrating a process of estimating a settled bioelectrical impedance value depending on bioelectrical impedance and electric skin resistance at a bio-processor of FIG. 7.

Referring to FIG. 8, a horizontal axis may represent the flow of time, and a vertical axis may represent resistance. A bioelectrical impedance value may be indicated by being classified as a floating time, a settling time, or a settled time. For convenience of description, a description will be given of FIG. 8 with reference to reference numerals of FIG. 7.

A dotted line of FIG. 8 indicates changes in measured bioelectrical impedance if a user sweats more than a general person. An alternate long and short dash line of FIG. 8 indicates changes in measured bioelectrical impedance if the user has a drier skin than a general person. A solid line of the FIG. 8 indicates changes in bioelectrical impedance which compensates a change in contact resistance according to a degree of skin dryness. The solid line, the dotted line, and the alternate long and short dash line shown in FIG. 8 may be understood as a graph simplified for convenience of description. A real degree of skin dryness may be changed in real time by stress or external stimulation.

Referring to FIG. 8, a floating time may be defined as a time before a first time point t1. In the floating time, bioelectrical impedance may have a floating impedance value FI4. Further, on a structure of a wearable device, a third electrode 223 and a fourth electrode 224 may maintain a state where the third electrode 223 and the fourth electrode 224 are in contact with the user, and a first electrode 221 and a second electrode 222 may be additionally in contact with the user when measuring bioelectrical impedance. As a contact time between the user and the third electrode 223 and the fourth electrode 224 is longer, the user may sweat a lot more. As the user sweat a lot more, since water or electrolyte having electrical conductivity is more generated, electric skin resistance may be reduced. Thus, electric skin resistance may continue being reduced during a floating time.

A settling time may be defined as a time between a first time point t1 and a sixth time point t6. A processing time may be defined as a time between the first time point t1 and a third time point t3 which is earlier than the sixth time point t6. Bioelectrical impedance may be reduced during the settling time. In case of a person who sweats a lot, as shown by a dotted line, electric skin resistance may be rapidly reduced. In case of a person who sweats a little, as shown by an alternate long and short dash line, electric skin resistance may be relatively gently reduced. As described above, during the processing time, a bioelectrical impedance sensor 231 may model changes in bioelectrical impedance as a fitting function. The bioelectrical impedance sensor 231 may estimate a bioelectrical impedance value at the sixth time point t6 based on the modeled fitting function.

In case of a person who sweats a lot, an estimated bioelectrical impedance value may indicate a first bioelectrical impedance value GIa. In case of a person who sweats a little, an estimated bioelectrical impedance value may indicate a second bioelectrical impedance value GIb.

As described above, the Galvanic skin response sensor 232 may measure electric skin resistance before bioelectrical impedance is measured the digital signal processor 235 may predict a contact time between an electrode unit 222 and a user based on the measured electric skin resistance. The digital signal processor 235 may predict electric skin resistance at the sixth time point t6 based on the predicted contact time. The digital signal processor 235 may compensate the first bioelectrical impedance value GIa or the second bioelectrical impedance value GIb to a compensated bioelectrical impedance value SI4 based on the electric skin resistance at the sixth time point t6.

The digital signal processor 235 may compensate the first bioelectrical impedance value GIa and/or the second bioelectrical impedance value GIb in a process of generating bio-data. For example, the digital signal processor 235 may compensate the measured first bioelectrical impedance value GIa and/or the measured second bioelectrical impedance value GIb to the compensated bioelectrical impedance value SI4 by using an electric skin resistance value determined by the Galvanic skin response sensor 232 as a parameter of regression data.

The digital signal processor 235 may compensate the first bioelectrical impedance value GIa and/or the second bioelectrical impedance value GIb to the compensated bioelectrical impedance value SI4 in a process of estimating a settled bioelectrical impedance value. For example, the digital signal processor 235 may model changes in bioelectrical impedance and may calculate a fitting function corresponding to a dotted line or an alternate long and short dash line, thus compensating the calculated fitting function to a fitting function corresponding to a solid line based on measured electric skin resistance. Alternatively, the digital signal processor 235 may model changes in bioelectrical impedance and may determine the first bioelectrical impedance value GIa and/or the second bioelectrical impedance value GIb as a settled bioelectrical impedance value, thus determining a final bioelectrical impedance value as the compensated bioelectrical impedance value SI4.

Figure 9:
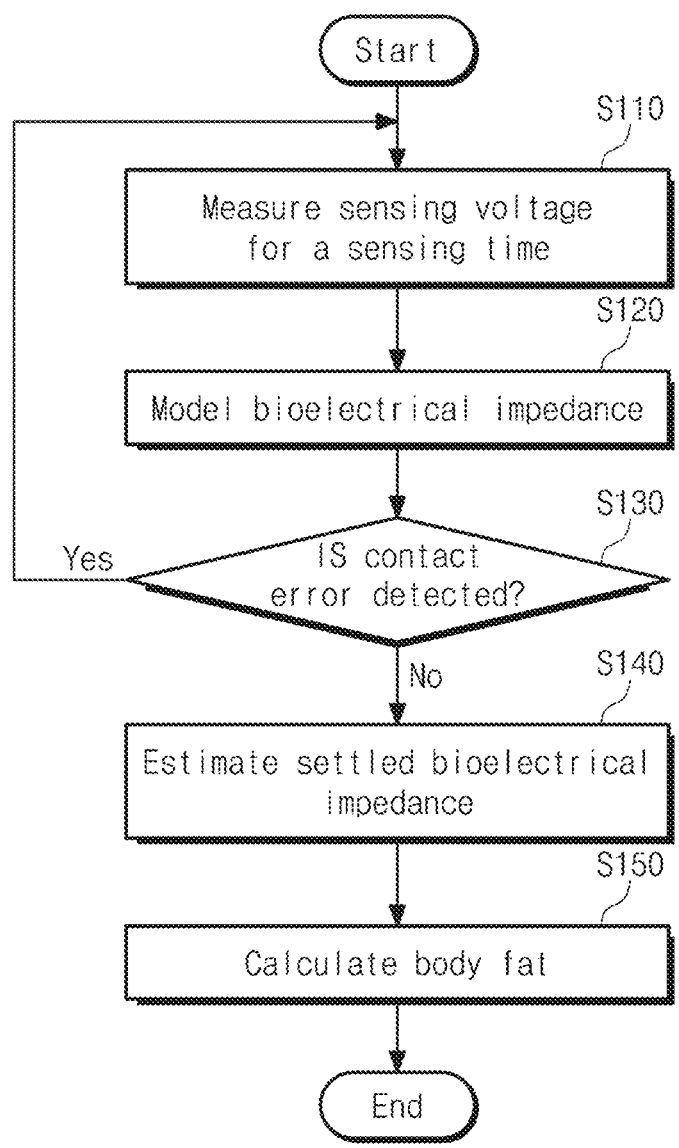
FIG. 9 is a flowchart illustrating an operation method of a bio-processor according to an example embodiment of the inventive concepts.

FIG. 9 is a flowchart illustrating an operation method of a bio-processor according to an example embodiment of the inventive concepts.

Referring to FIG. 9, the operation method of the bio-processor may be performed by a bio-processor 130 of FIG. 1 or 2 or a bio-processor 230 of FIG. 7. For convenience of description, a description will be given of FIG. 9 with reference to reference numerals of FIG. 2.

In operation S110, the bioelectrical impedance sensor 131 may measure a sensing voltage during a sensing time. The bioelectrical impedance sensor 131 may receive a sensing voltage Vsen from an electrode unit 120. The bioelectrical impedance sensor 131 may measure bioelectrical impedance for the user using an output current Iout supplied to a user and the sensing voltage Vsen supplied from the user. The sensing time may include a portion of a settling time. The digital signal processing 134 may control the length of the sensing time such that the sensing time may be shorter than the settling time.

In operation S120, the digital signal processor 134 may model bioelectrical impedance. The digital signal processor 134 may model bioelectrical impedance measured during the sensing time as a fitting function. The fitting function may be a function which has linearity over time, for example, a natural logarithmic function. The fitting function may indicate an approximate value of bioelectrical impedance at the settling time. The digital signal processor 134 may determine a coefficient or a constant of a fitting function having the nearest value to a value of measured bioelectrical impedance.

In operation S130, the digital signal processor 134 may determine a contact error. The digital signal processor 134 may compare the modeled fitting function with measured bioelectrical impedance. The digital signal processor 134 may accumulate and calculate a difference between the fitting function and real bioelectrical impedance at a corresponding time. If the accumulated and calculated result is greater than an error reference value, the digital signal processor 134 may determine that a contact error occurs between the user and an electrode unit 120. If the contact error is detected, a bio-signal detecting system 100 may provide a visual or auditory message for requesting to maintain a contact state with the electrode unit 120 to the user. Thereafter, operation S110 may progress again. If the contact error is not detected, operation S140 may progress.

In operation S140, the digital signal processor 134 may estimate a settled bioelectrical impedance value. The digital signal processor 134 may estimate the settled bioelectrical impedance value based on the fitting function modeled in operation S120. For example, the digital signal processor 134 may determine a settled time of a bioelectrical impedance value based on the modeled fitting function. The digital signal processor 134 may estimate a fitting function value of the settled time as the settled bioelectrical impedance value.

As shown in FIG. 7, if the bio-processor 230 includes a Galvanic skin response sensor 232, in operation S140, contact resistance of a settled time, calculated as a result of measuring electric skin resistance, may be reflected in a settled bioelectrical impedance value. In other words, the digital signal processor 235 of FIG. 7 may calculate a contact resistance value between the user and the electrode unit 220 based on electric skin resistance measured by the Galvanic skin response sensor 232. The digital signal processor 235 may reflect a contact resistance value in the settled bioelectrical impedance value to remove additional resistance generated by sweat or the like.

In operation S150, the digital signal processor 134 may calculate body fat based on the estimated bioelectrical impedance value. The digital signal processor 134 may apply the estimated bioelectrical impedance value to a regression equation to calculate the body fat. The digital signal processor 134 may additionally apply user information about a height, a weight, an age, or a gender as well as the bioelectrical impedance to the regression equation to calculate the body fat. The user information and information about the regression equation may be previously stored in a nonvolatile memory 135. Operation 150 is specified to calculate the body fat. However, example embodiments are not limited thereto. For example, the digital signal processor 134 may calculate a variety of body composition based on the settled bioelectrical impedance value.

Figure 10:
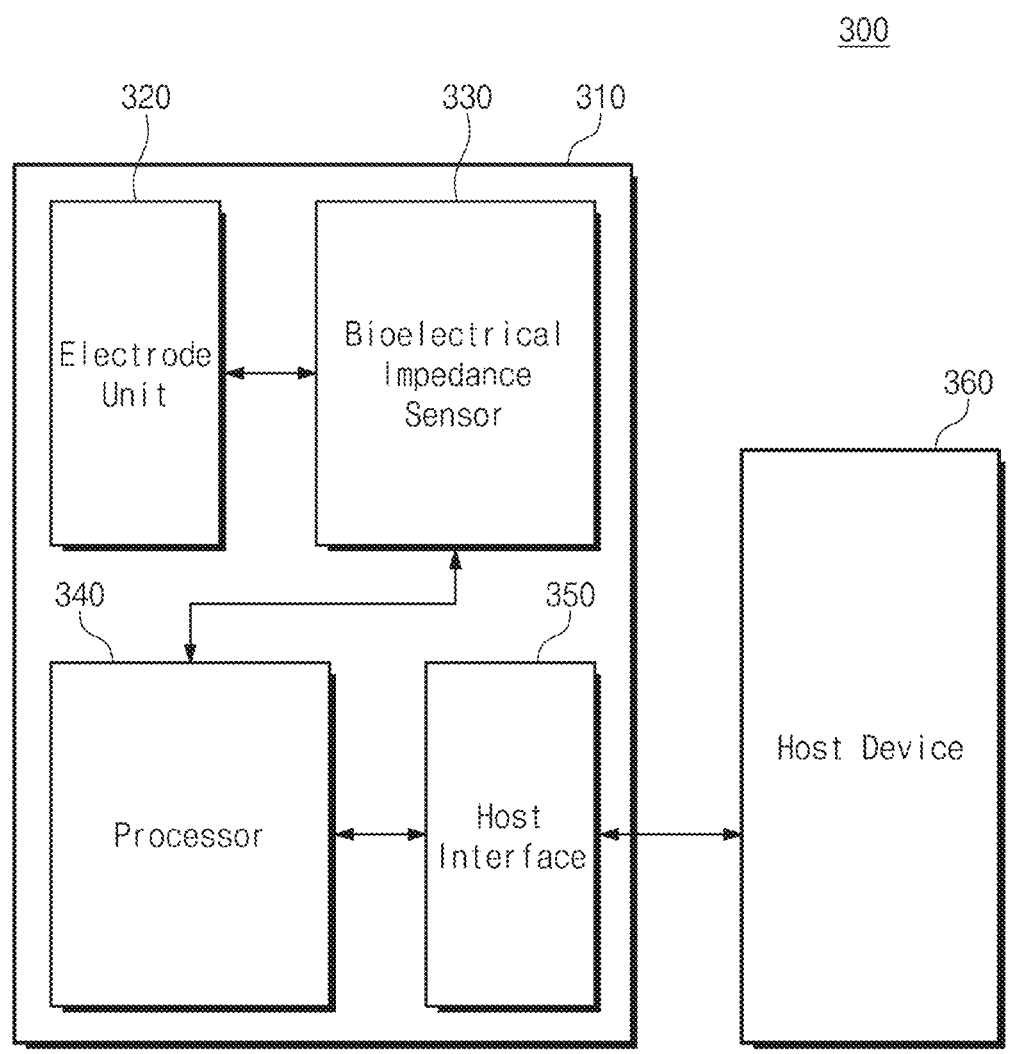
FIG. 10 is a block diagram illustrating a configuration of a bio-signal detecting system according to an example embodiment of the inventive concepts.

FIG. 10 is a block diagram illustrating a configuration of a bio-signal detecting system according to an example embodiments of the inventive concepts. A bio-signal detecting system 100 of FIG. 1 may process a process of sensing bioelectrical impedance and generating bio-data based on the sensed bioelectrical impedance in an integrated manner using a bio-processor 130. A bio-signal detecting system 300 of FIG. 10 may separately provide a configuration of sensing bioelectrical impedance and a configuration of generating bio-data based on the bioelectrical impedance.

Referring to FIG. 10, the bio-signal detecting system 300 may include a bio-signal detecting device 310 and a host device 360. The bio-signal detecting device 310 may include an electrode unit 320, a bioelectrical impedance sensor 330, a processor 340, and a host interface 350. Since the electrode unit 320 has the same configuration as an electrode unit 120 of FIG. 1 and performs the same function as the electrode unit 120, a detailed description will be omitted.

The bioelectrical impedance sensor 330 may measure bioelectrical impedance during a sensing time. The bioelectrical impedance sensor 330 may supply an output current to a user through the electrode unit 320. For this purpose, the bioelectrical impedance sensor 330 may include a current generator. The bioelectrical impedance sensor 330 may receive a sensing voltage generated by the output current through the user, via the electrode unit 320. The bioelectrical impedance sensor 330 may measure bioelectrical impedance for the user based on the received sensing voltage. The bioelectrical impedance sensor 330 may perform the same function as a bioelectrical impedance sensor 131 of FIG. 2.

The processor 340 may estimate a settled bioelectrical impedance value based on bioelectrical impedance measured during a sensing time. The processor 340 may model bioelectrical impedance measured during the sensing time as a fitting function. The processor 340 may determine a coefficient or a constant of the fitting function to be nearest to measured bioelectrical impedance. The processor 340 may estimate a bioelectrical impedance value of a settled time based on a determined fitting function. Further, the processor 340 may compare the fitting function with the measured bioelectrical impedance to determine a contact error. The operation of estimating the settled bioelectrical impedance value of the processor 340 may be the same as that of a digital signal processor 134 of FIG. 2.

The processor 340 may generate bio-data based on the estimated bioelectrical impedance value. The processor 340 may apply a settled bioelectrical impedance value to regression data. The processor 340 may apply a parameter including a settled bioelectrical impedance value and user data to the regression data to generate bio-data. The user data may be received from the host device 360 through the host interface 350. The processor 340 may provide bio-data to the host device 360 through the host interface 350 depending on a request of the host device 360. The process of generating the bio-data at the processor 340 may be the same as that of a digital signal processor 134 of FIG. 2.

The host interface 350 may provide an interface between the host device 360 and the bio-signal detecting device 310. The host interface 350 may communicate with the host device 360 using a universal serial bus (USB), a small computer system interface (SCSI), a peripheral component interconnect (PCI) express, ATA, parallel ATA (PATA), serial ATA (SATA), a serial attached SCSI (SAS), or the like.

The host device 360 may communicate with the bio-signal detecting device 310 through the host interface 350. The host device 360 may provide query data for requesting to provide bio-data to the bio-signal detecting device 310. In this case, the host device 360 may receive the bio-data from the bio-signal detecting device 310. For this purpose, the host device 360 may provide user data to the bio-signal detecting device 310. The host device 360 may include various electronic devices such as a computer device, a smartphone, or a portable terminal.

Figure 11:
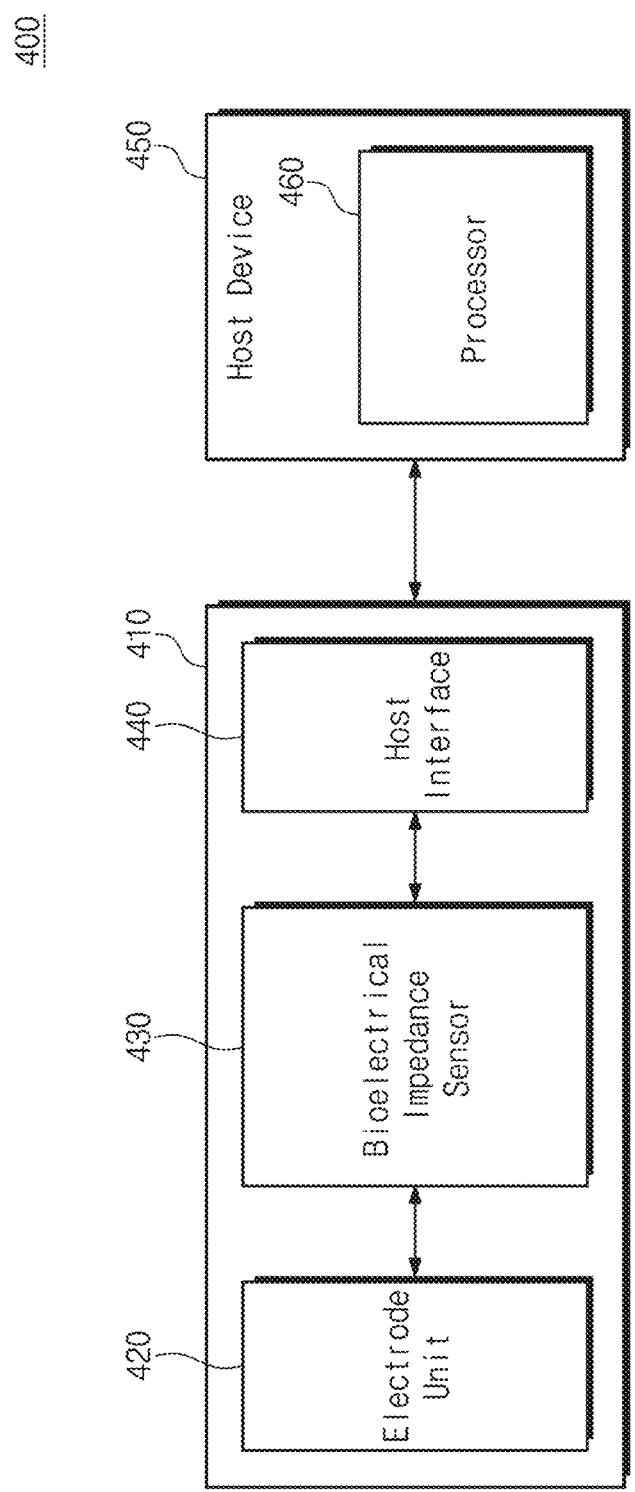
FIG. 11 is a block diagram illustrating a configuration of a bio-signal detecting system according to an example embodiment of the inventive concepts.

FIG. 11 is a block diagram illustrating a configuration of a bio-signal detecting system according to an example embodiment of the inventive concepts.

Referring to FIG. 11, a bio-signal detecting system 400 of FIG. 11 may separately provide a configuration of sensing bioelectrical impedance and a configuration of generating bio-data based on the bioelectrical impedance.

The bio-signal detecting system 400 may include a bio-signal detecting device 410 and a host device 450. The bio-signal detecting device 410 may include an electrode unit 420, a bioelectrical impedance sensor 430, and a host interface 440. The host device 450 may include a processor 460.

Since the electrode unit 420 has the same configuration as an electrode unit 120 of FIG. 1 or an electrode 320 of FIG. 10 and performs the same function as the electrode unit 120 or the electrode 320, a detailed description will be omitted. Since the bioelectrical impedance sensor 430 has the same configuration as a bioelectrical impedance sensor 330 of FIG. 10 and performs the same function as the bioelectrical impedance sensor 330, a detailed configuration will be omitted. The host interface 440 may have the same configuration as a host interface 350 of FIG. 10 and may perform the same function as the host interface 350. The host interface 440 may transmit information about bioelectrical impedance measured during a sensing time by the bioelectrical impedance sensor 430 to the host device 450.

The host device 450 may communicate with the bio-signal detecting device 410 through the host interface 440. The host device 450 may provide query data for requesting to provide bioelectrical impedance information to the bio-signal detecting device 410. In this case, the host device 450 may receive the bioelectrical impedance information from the bio-signal detecting device 410.

The processor 460 may estimate a settled bioelectrical impedance value based on the bioelectrical impedance information received from the bio-signal detecting device 410. The processor 460 may model bioelectrical impedance measured by the bioelectrical impedance sensor 430 as a fitting function. The processor 460 may estimate a bioelectrical impedance value of a settled time based on the fitting function. The processor 460 may generate bio-data based on a settled bioelectrical impedance value. The processor 460 may perform the same function as a processor 340 of FIG. 10 or a digital signal processor 134 of FIG. 2.

Figure 12:
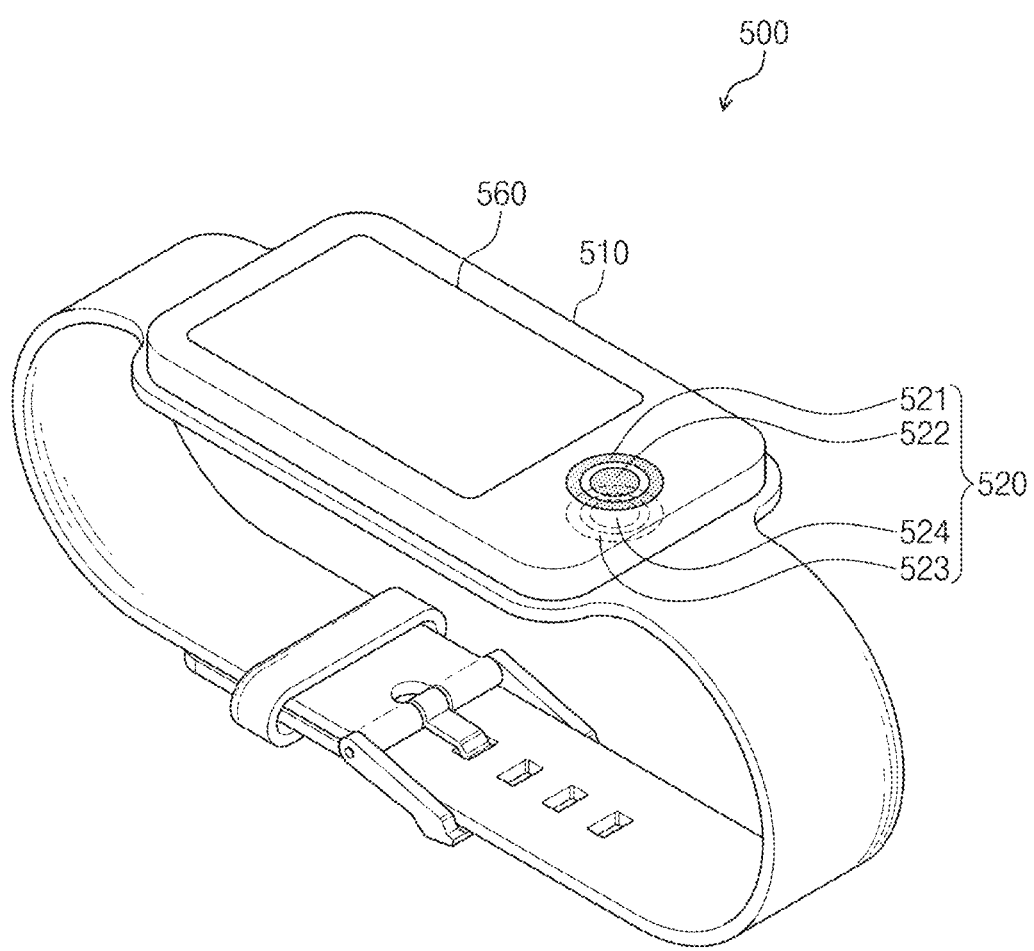
FIG. 12 is a drawing illustrating a configuration of a wearable device according to an example embodiment of the inventive concepts.

FIG. 12 is a drawing illustrating a configuration of a wearable device according to an example embodiment of the inventive concepts.

Referring to FIG. 12, a wearable device 500 of FIG. 12 may be configured to be worn on a wrist of a user. A bio-signal detecting system 100 of FIG. 1 may be implemented in the wearable device 500 of FIG. 12. Alternatively, a bio-signal detecting device 310 of FIG. 10 or a bio-signal detecting device 410 of FIG. 11 may be implemented in the wearable device 500.

The wearable device 500 may include a processor 510, an electrode unit 520, and a display 560.

The processor 510 may be embedded in the wearable device 500. The processor 510 may measure bioelectrical impedance and may generate bio-data. In this case, the processor 510 may be, but is not limited to, a bio-processor 130 of FIG. 2 or a bio-processor 230 of FIG. 7. For example, the processor 510 may estimate a settled bioelectrical impedance value based on measured bioelectrical impedance and may generate bio-data. In this case, the processor 510 may be a processor 340 of FIG. 10, and the wearable device 500 may separately include a bioelectrical impedance sensor.

The electrode unit 520 may include first to fourth electrodes 521 to 524. The first electrode 521 and the second electrode 522 may be located to be adjacent to a display surface of the display 560 included in the wearable device 500. In other words, the first electrode 521 and the second electrode 522 may fail to be in contact with the wrist when the user wears the wearable device 500. The first electrode 521 and the second electrode 522 may be located to be adjacent to each other and may be insulated from each other. The third electrode 523 and the fourth electrode 524 may be located on a contact surface of the wrist with the wearable device 500. In other words, the third electrode 523 and the fourth electrode 524 may be in contact with the wrist when the user wears the wearable device 500. The third electrode 523 and the fourth electrode 524 may be located to be adjacent to each other and may be insulated from each other.

If the wearable device 500 is worn on a left wrist of the user, to measure bioelectrical impedance, the user brings his or her right hand into contact with the first electrode 521 and the second electrode 522. In this case, the second electrode 522 (or a first electrode 521) and the fourth electrode 524 (or the third electrode 523) may form a closed circuit through a body of the user. The processor 510 may measure bioelectrical impedance using a potential difference by an output current which flows via the closed circuit, for example, a sensing voltage.

The display 560 may display information associated with bio-data generated according to measured bioelectrical impedance. Further, if a contact state between the user and the electrode unit 520 is bad as the determined result of the processor 510, the display 560 may display a message for requesting the user to maintain a contact state with the electrode unit 520. The wearable device 500 may further include a speaker (not shown) for auditorily providing information associated with bio-data or a message for requesting to maintain a contact state.

Although not illustrated in detail, the wearable device 500 may further include various elements for measuring bioelectrical impedance and generating, displaying, and transmitting bio-data such as body fat data. For example, the wearable device 500 may further include a processor 140, a storage device 170, a memory 180, and a modem of FIG. 1.

The bio-processor, the bio-signal detecting system, and an operation method of the bio-processor may reduce a time when a bio-signal is measured, by estimating a settled bioelectrical impedance value based on bioelectrical impedance of a settling time, thus ensuring accuracy of the settled bioelectrical impedance value.

While the inventive concepts have been described with reference to some example embodiments, it will be apparent to those skilled in the art that various changes and modifications may be made without departing from the spirit and scope of the inventive concepts. Therefore, it should be understood that the above example embodiments are not limiting, but illustrative.

What is claimed is:

1. A bio-processor, comprising:
    a bioelectrical impedance sensor configured to measure changes in a first impedance value at a first time point and a second impedance value at a second time point later than the first time point, the second time point being a settled time point; and
    a digital signal processor configured to:
        receive a portion of the changes from the bioelectrical impedance sensor, wherein the portion corresponds to a first period between the first time point and a third time point, the third time point being later than the first time point and earlier than the second time point;
        estimate the second impedance value before the second time point, based on the received portion of the changes; and
        generate bio-data based on the estimated second impedance value.

2. The bio-processor of claim 1, wherein the first impedance value is larger than the second impedance value, and a third impedance value at the third time point is larger than the second impedance value.

3. The bio-processor of claim 1, wherein the digital signal processor is configured to:
    model the portion of the changes as a fitting function corresponding to a second period between the first and the second time points; and
    estimate the second impedance value based on the modeled fitting function.

4. The bio-processor of claim 3, wherein the digital signal processor is further configured to:
    calculate a fourth time point at which a measured impedance value first reaches a settled impedance value, based on the modeled fitting function, the fourth time point being earlier than the second time point and later than the third time point; and
    estimate the settled impedance value based on the fourth time point and the modeled fitting function,
        wherein the settled impedance value is equal to the second impedance value.

5. The bio-processor of claim 3, wherein the modeled fitting function is a natural logarithmic function.

6. The bio-processor of claim 3, wherein the digital signal processor is configured to:
    estimate the changes based on the modeled fitting function;
    accumulate differences with the measured changes of the bioelectrical impedance sensor and the estimated changes of the digital signal processor;
    determine whether a result of the accumulated differences is greater than a reference value; and
    request the bioelectrical impedance sensor to measure changes in a fifth impedance value at a fifth time point being later that the second time point and a sixth impedance value at a sixth time point being later than the fifth time point, if it is determined that the result of the accumulated differences is greater than the reference value.

7. The bio-processor of claim 1, wherein the digital signal processor is configured to:
    generate the bio-data based on a parameter included in the estimated second impedance value such that the bio-data generated by the digital signal processor includes body fat data.

8. The bio-processor of claim 7, further comprising:
    a nonvolatile memory configured to store parameter data and regression data, the parameter data including information about a value of the parameter and the regression data including data used to calculate the bio-data from the value of the parameter.

9. The bio-processor of claim 1, further comprising:
    a Galvanic skin response sensor configured to measure electric skin resistance by a Galvanic skin response before the second time point, and
    wherein the digital signal processor is configured to:
        estimate a contact resistance value at the second time point based on the measured electric skin resistance; and
        compensate the estimated second impedance value based on the estimated contact resistance value.

10. A bio-processor, comprising:
    a bioelectrical impedance sensor configured to measure changes in impedance values in a sensing period, wherein the sensing period includes a settling period and a settled period;
    a digital signal processor configured to:
        receive a portion of the changes in the settling period from the bioelectrical impedance sensor;
        estimate a settled impedance value of the settled period during the settling period, based on the received portion of the changes; and
        generate bio-data based on the estimated settled impedance value prior to the settled period.

11. The bio-processor of claim 10, wherein a first impedance value of a start time point of the settling period is larger than second impedance value of an end time point of the settling period,
    wherein a third impedance value of a start time point of the settled period is equal to a fourth impedance value of an end time point of the settled period, and the impedance values in the settled period correspond to the settled impedance value and the settled period is later that the settling period.

12. The bio-processor of claim 10, wherein the digital signal processor is configured to:
    model the portion of the changes as a fitting function corresponding to the settling period; and
    estimate the settled impedance value based on the modeled fitting function.

13. The bio-processor of claim 12, wherein the digital signal processor is configured to:
    calculate a time point at which a measured impedance value first reaches the settled impedance value, based on the modeled fitting function; and
    estimate the settled impedance value based on the time point and the modeled fitting function.

14. The bio-processor of claim 12, wherein the modeled fitting function is a natural logarithmic function.

15. The bio-processor of claim 12, wherein the digital signal processor is configured to:

determine a contact error between the bioelectrical impedance sensor and a user, by comparing the modeled fitting function with the measured changes.

16. The bio-processor of claim 10, wherein the digital signal processor is configured to:
generate the bio-data based on a parameter included in the settled impedance value such that the bio-data generated by the digital signal processor includes body fat data.

17. The bio-processor of claim 10, further comprising:
a nonvolatile memory configured to store parameter data and regression data, the parameter data including information about a value of a parameter and the regression data including data used to calculate the bio-data from the value of the parameter.

18. A method of operating a bio-processor, the method comprising:
measuring changes in a first impedance value at a first time point and a second impedance value at a second time point later than the first time point, the second time point being a settled time point;
receiving a portion of the changes from a bioelectrical impedance sensor, wherein the portion is corresponding to a time period between the first time point and a third time point, the third time point being later than the first time point and earlier than the second time point;
estimating the second impedance value before the second time point, based on the received portion of the changes; and
generating bio-data based on the estimated second impedance value.

19. The method of claim 18, further comprising:
modeling the portion of the changes as a fitting function; and
estimating the second impedance value based on the modeled fitting function.

20. The method of claim 19, further comprising:
calculating a fourth time point at which a measured impedance value first reaches a settled impedance value, based on the modeled fitting function, the fourth time point being earlier than the second time point and later than the third time point; and
estimating the settled impedance value based on the fourth time point and the modeled fitting function,
wherein the settled impedance value is equal to the second impedance value.

* * * * *